US006312867B1

(12) United States Patent
Kinsho et al.

(10) Patent No.: US 6,312,867 B1
(45) Date of Patent: Nov. 6, 2001

(54) ESTER COMPOUNDS, POLYMERS, RESIST COMPOSITIONS AND PATTERNING PROCESS

(75) Inventors: Takeshi Kinsho; Tsunehiro Nishi, both of Nakakubiki-gun; Hideshi Kurihara, Usui-gun; Koji Hasegawa, Nakakubiki-gun; Takeru Watanabe, Nakakubiki-gun; Osamu Watanabe, Nakakubiki-gun; Mutsuo Nakashima, Nakakubiki-gun; Takanobu Takeda, Nakakubiki-gun; Jun Hatakeyama, Nakakubiki-gun, all of (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/431,139

(22) Filed: Nov. 1, 1999

(30) Foreign Application Priority Data

Nov. 2, 1998 (JP) ........................................ 10-312533
Mar. 19, 1999 (JP) ........................................ 11-075355

(51) Int. Cl.[7] ........................................ G03F 7/004

(52) U.S. Cl. ...................... 430/270.1; 430/325; 560/205; 560/220; 526/271; 526/281; 526/313; 526/319; 526/321; 526/347; 526/329.7

(58) Field of Search ................................ 430/270.1, 325; 568/820; 560/120, 205, 220; 526/281, 319, 321, 313, 347, 271

(56) References Cited

U.S. PATENT DOCUMENTS

| | | | | |
|---|---|---|---|---|
| 4,841,005 | * | 6/1989 | Tamaru et al. | 526/245 |
| 5,069,997 | | 12/1991 | Schwalm et al. | 430/270 |
| 5,230,984 | * | 7/1993 | Tachiki et al. | 430/270 |
| 5,585,222 | | 12/1996 | Kaimoto et al. | 430/296 |
| 5,929,271 | * | 7/1999 | Hada et al. | 560/126 |
| 6,147,177 | * | 11/2000 | Jararaman et al. | 526/281 |
| 6,153,785 | * | 11/2000 | Jung | 560/120 |

FOREIGN PATENT DOCUMENTS

| | | | |
|---|---|---|---|
| 2-19847 | | 1/1990 | (JP) . |
| 4-215661 | | 8/1992 | (JP) . |
| 5-80515 | | 4/1993 | (JP) . |
| 5-88367 | | 4/1993 | (JP) . |
| 11-84663 | * | 3/1999 | (JP) . |
| 11-271974 | * | 10/1999 | (JP) . |

OTHER PUBLICATIONS

CAPLUS citation of JP 11084663, Mar. 1999.*

"Diastereoselective Nitrile Oxide and Nitrone Additions", Olsson, T. et al, Tetrahedron, 46(7), 2473–2482, 1990.*

Derwent abstract of KR 98064842, Oct. 1998.*

JPAB abstract of JP 11084663, Mar. 1999.*

Derwent abstract of JP 11084663, Mar. 1999.*

CAPLUS and Derwent abstracts of JP 11–271974, Oct. 1999 131:264782.*

Allen, Robert D. et al., "Single Layer Resists with Enhanced Etch Resistance for 193 nm Lithography," *Journal of Photopolymer Science and Technology*, vol. 7, No. 3, pp. 507–516 (1994).

English abstract for JP–5088367.

English abstract for JP–4215661.

* cited by examiner

*Primary Examiner*—Rosemary E. Ashton
(74) *Attorney, Agent, or Firm*—Millen, White, Zelano & Branigan, P.C.

(57) ABSTRACT

A novel ester compound having an exo-form 2-alkylbicyclo [2.2.1]heptan-2-yl group as the protective group is provided as well as a polymer comprising units of the ester compound. The polymer is used as a base resin to formulate a resist composition having a higher sensitivity, resolution and etching resistance than conventional resist compositions.

17 Claims, No Drawings

ESTER COMPOUNDS, POLYMERS, RESIST COMPOSITIONS AND PATTERNING PROCESS

BACKGROUND OF THE INVENTION

1. Field of the Invention

The present invention relates to (1) a novel ester compound, (2) a polymer comprising units of the ester compound which is blended as a base resin to formulate a resist composition having a high sensitivity, resolution and etching resistance, and in particular, suitable as micropatterning material for VLSI fabrication, (3) a method for preparing the polymer, (4) a resist composition comprising the polymer, and (5) a patterning process using the resist composition.

2. Prior Art

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 $\mu$m or less.

For resist materials for use with a KrF excimer lasers, polyhydroxystyrene having a practical level of transmittance and etching resistance is, in fact, a standard base resin. For resist materials for use with a ArF excimer lasers, polyacrylic or polymethacrylic acid derivatives and polymers comprising aliphatic cyclic compounds in the backbone are under investigation. In either case, the basic concept is that some or all of alkali soluble sites of alkali soluble resin are protected with acid labile or eliminatable groups. The overall performance of resist material is adjusted by a choice from among a variety of acid eliminatable protective groups.

Exemplary acid eliminatable protective groups include tert-butoxycarbonyl (JP-B 2-27660), tert-butyl (JP-A 62-115440 and J. Photopolym. Sci. Technol. 7 [3], 507 (1994)), 2-tetrahydropyranyl (JP-A 5-80515 and 5-88367), and 1-ethoxyethyl (JP-A 2-19847 and 4-215661). While it is desired to achieve a finer pattern rule, none of these acid eliminatable protective groups are deemed to exert satisfactory performance.

More particularly, tert-butoxycarbonyl and tert-butyl are extremely less reactive with acids so that a substantial quantity of energy radiation must be irradiated to generate a sufficient amount of acid in order to establish a difference in rate of dissolution before and after exposure. If a photoacid generator of the strong acid type is used, the exposure can be reduced to a relatively low level because reaction can proceed with a small amount of acid generated. However, in this event, the deactivation of the generated acid by airborne basic substances has a relatively large influence, giving rise to such problems as a T-top pattern. On the other hand, 2-tetrahydropyranyl and 1-ethoxyethyl are so reactive with acids that with the acid generated by exposure, elimination reaction may randomly proceed without a need for heat treatment, with the result that substantial dimensional changes occur between exposure and heat treatment/development. Where these groups are used as protective groups for carboxylic acid, they have a low dissolution inhibiting effect to alkali, resulting in a high rate of dissolution in unexposed areas and film thinning during development. If highly substituted polymers are used to avoid such inconvenience, there results an extreme drop of heat resistance. These resins fail to provide a difference in rate of dissolution before and after exposure, resulting in resist materials having a very low resolution.

SUMMARY OF THE INVENTION

Therefore, an object of the present invention is to provide (1) a novel ester compound capable of forming an acid-decomposable polymer, (2) a polymer which is blended as a base resin to formulate a resist composition having a higher sensitivity, resolution and etching resistance than conventional resist compositions, (3) a method for preparing the polymer, (4) a resist composition comprising the polymer as a base resin, and (5) a patterning process using the resist composition.

The inventor has found that a novel ester compound of the following general formula (1) obtained by the method to be described later is useful in preparing an acid-decomposable polymer; that a resist composition comprising as the base resin a novel polymer prepared from the ester compound to a weight average molecular weight of 1,000 to 500,000 has a high sensitivity, resolution and etching resistance; and that this resist composition lends itself to precise micropatterning.

In a first aspect, the invention provides an ester compound of the following general formula (1):

(1)

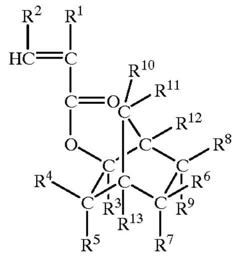

wherein $R^1$ is hydrogen, methyl or $CH_2CO_2R^{14}$; $R^2$ is hydrogen, methyl or $CO_2R^{14}$; $R^3$ is a straight, branched or cyclic alkyl group of 1 to 8 carbon atoms or a substituted or unsubstituted aryl group of 6 to 20 carbon atoms; $R^4$ to $R^{13}$ each are hydrogen or a monovalent hydrocarbon group of 1 to 15 carbon atoms which may contain a hetero atom and $R^4$ to $R^{13}$, taken together, may form a ring, and when they form a ring, they represent divalent hydrocarbon groups of 1 to 15 carbon atoms which may contain a hetero atom, or two of $R^4$ to $R^{13}$ which are attached to adjacent carbon atoms may directly bond together to form a double bond; and R14 is a straight, branched or cyclic alkyl of 1 to 15 carbon atoms. The formula also represents an enantiomer.

In a second aspect, the invention provides a polymer comprising units of an ester compound of the following general formula (la) and having a weight average molecular weight of 1,000 to 500,000.

(1a)

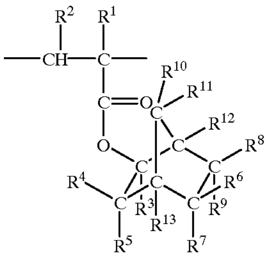

$R^1$ to $R^{13}$ are as defined above. The formula also represents an enantiomer.

The polymer may further comprises recurring units of at least one of the following formulae (2a) to (13a):

(2a)

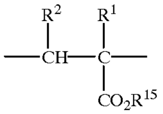

(3a)

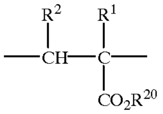

(4a)

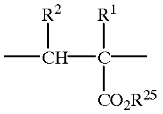

(5a)

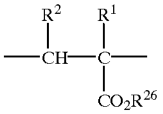

(6a)

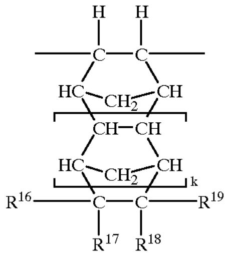

(7a)

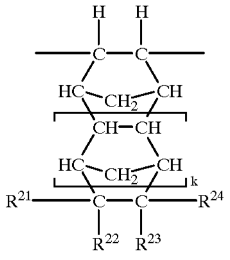

-continued (8a)

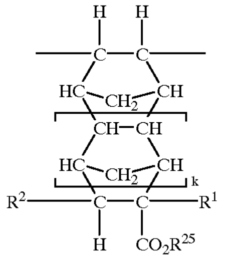

(9a)

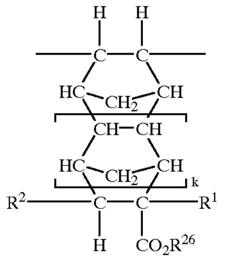

(10a)

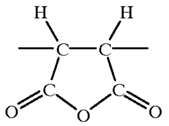

(11a)

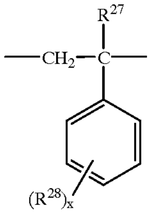

(12a)

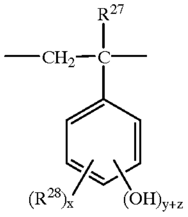

(13a)

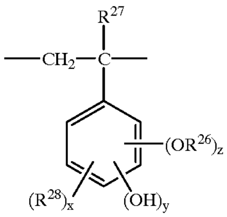

wherein $R^1$ and $R^2$ are as defined above; $R^{15}$ is hydrogen or a monovalent hydrocarbon group of 1 to 15 carbon atoms containing a carboxyl or hydroxyl group; at least one of $R^{16}$ to $R^{19}$ represents a monovalent hydrocarbon group of 1 to 15 carbon atoms containing a carboxyl or hydroxyl group, and the remaining of $R^{16}$ to $R^{19}$ independently represent hydrogen or a straight, branched or cyclic alkyl group of 1 to 15 carbon atoms, or $R^{16}$ to $R^{19}$, taken together, may form a ring with the proviso that at least one of $R^{16}$ to $R^{19}$ represents a divalent hydrocarbon group of 1 to 15 carbon atoms containing a carboxyl or hydroxyl group, and the remaining of $R^{16}$ to $R^{19}$ independently represent a straight, branched or cyclic alkylene group of 1 to 15 carbon atoms; $R^{20}$ is a monovalent hydrocarbon group of 3 to 15 carbon atoms containing a —$CO_2$— partial structure; at least one of $R^{21}$ to $R^{24}$ represents a monovalent hydrocarbon group of 2 to 15 carbon atoms containing a —$CO_2$— partial structure, and the remaining of $R^{21}$ to $R^{24}$ independently represent hydrogen or a straight, branched or cyclic alkyl group of 1 to 15 carbon atoms, or $R^{21}$ to $R^{24}$, taken together, may form a ring with the proviso that at least one of $R^{21}$ to $R^{24}$ represents a divalent hydrocarbon group of 1 to 15 carbon atoms containing a —$CO_2$— partial structure, and the remaining of $R^{21}$ to $R^{24}$ independently represent a straight, branched or cyclic alkylene group of 1 to 15 carbon atoms; $R^{25}$ is a polycyclic hydrocarbon group of 7 to 15 carbon atoms or an alkyl group containing a polycyclic hydrocarbon group; $R^{26}$ is an acid labile group; $R^{27}$ is hydrogen or methyl; $R^{28}$ is a straight, branched or cyclic alkyl group of 1 to 8 carbon atoms; k is equal to 0 or 1, and x, y and z are integers of 0 to 3, satisfying $x+y+z \leqq 5$ and $1 \leqq y+z$.

In a third aspect, the invention provides a method for preparing a polymer comprising the step of effecting radical polymerization, anionic polymerization or coordination polymerization between an ester compound of formula (1) and another compound having a carbon-to-carbon double bond.

In a fourth aspect, the invention provides a resist composition comprising the polymer defined above, and preferably a photoacid generator, and an organic solvent.

In a fifth aspect, the invention provides a process for forming a pattern, comprising the steps of applying the resist composition defined above onto a substrate to form a coating; heat treating the coating and exposing the coating to high energy radiation or electron radiation through a photomask; optionally heat treating the exposed coating, and developing the coating with a developer.

The ester compound of formula (1) and the polymer comprising units of formula (1a) employ an exo-form 2 -alkylbicyclo[2.2.1]heptan-2-yl group or derivative thereof as the acid-eliminatable protective group, thereby overcoming the problems including the tert-butoxycarbonyl and tert-butyl groups having low reactivity with acid as well as the 2-tetrahydropyranyl and 1-ethoxyethyl groups having too high reactivity with acid and low resistance to alkaline developers.

The ester compounds of formula (1) are broadly classified as alkylcycloalkyl esters. The alkylcycloalkyl esters being basically tertiary alkyl esters are free of the drawbacks of excessive acidolysis and ease of dissolution in basic developer; when formulated into resist materials, they do not allow for the infinite progress of decomposition between exposure and development and film thinning during development; nevertheless, they have higher acidolysis than simple tertiary alkyl esters such as tert-butyl esters. For these reasons, the alkylcycloalkyl esters belong to a relatively satisfactory class of acid labile sites. The ester compounds of formula (1) and the polymers comprising units of formula (1a) are successful in significantly enhancing acidolysis without compromising the advantages of the alkylcycloalkyl esters. The reason is given below.

Decomposition reaction of tertiary alkyl esters under acidic conditions proceeds by way of E1 mechanism. Those esters having a more stable carbocation under transition conditions have a higher rate of reaction and hence, a higher rate of decomposition. In the exo-form 2-alkylbicyclo[2.2.1]heptan-2-yl esters of formula (1), probably because of σ-participation, a very stable cation is formed as shown by the reaction scheme below, and thus the progress of reaction is very rapid. This is a reaction inherent to the exo-form compound of formula (1). Little or no reaction occurs with an isomer or an endo-form compound of the following formula (1'). The compounds of formulae (1) and (1'), which look alike when expressed in plan structure, have largely different rates of acid decomposition reaction. Accordingly, the compound of formula (1), the compound of formula (1'), and the compound of formula (1") expressed with no stereostructure taken into account must be recognized, in fact, to be completely different substances (see Y. Yukawa Ed., Theory of Organic Chemistry -Reaction-, Kagaku Dojin Publishing, 1974, Chap.

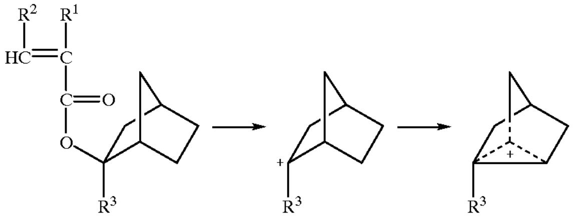

(1)

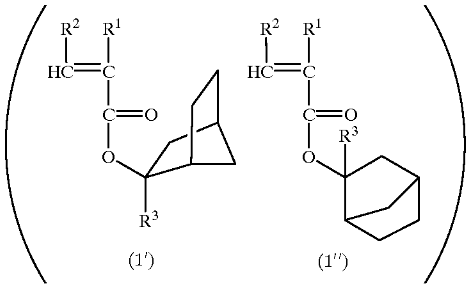

(1') (1'')

Herein, $R^1$ to $R^{13}$ are as defined above although $R^4$ to $R^{13}$ are omitted for the brevity of description.

Because of the above-described mechanism, the exo-form 2-alkylbicyclo[2.2.1]heptan-2-yl esters of formula (1) have an acid decomposition ability that outstandingly surpasses not only simple tertiary alkyl esters, but also alkylcycloalkyl esters and prior art fused ring-containing alkylcycloalkyl esters having not considered stereo-chemistry. Therefore, the resist composition comprising as a base resin a polymer originating from the inventive compound becomes a very high sensitivity resist material as compared with prior art resist materials, as will be later demonstrated in Examples.

Although the compounds of formula. (1) have been arrived at originally from efforts in pursuit of acid decomposition, quite unexpectedly, they have some advantages in addition to high reactivity. Such advantages are a large polarity change due to the high hydrophobic nature of an eliminatable portion of the acid eliminatable group, and a very high rigidity that bicyclo[2.2.1]heptane skeleton possesses. Because of these excellent characteristics, the resist composition of the invention has a high resolution and very high etching resistance as well as high sensitivity.

The ester compounds of formula (1) have been arrived at by making investigations on acid elimination reaction from the aspect of stereochemistry. In this sense, the present invention is based on a concept utterly different from the prior art improvement in acid eliminatable groups that was discussed solely from the standpoint of plane structure. The invention is clearly distinguishable from the prior art proposals of novel acid eliminatable groups.

DETAILED DESCRIPTION OF THE INVENTION

Ester Compound

The novel ester compounds according to the first aspect of the invention are of the following general formula (1).

(1)

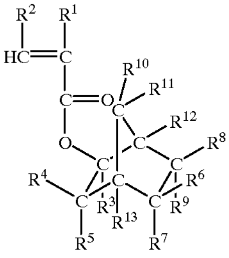

Herein, $R^1$ is hydrogen, methyl or $CH_2CO_2R^{14}$ wherein $R^{14}$ is illustrated later. $R^2$ is hydrogen, methyl or $CO_2R^{14}$. $R^3$ is a straight, branched or cyclic alkyl group of 1 to 8 carbon atoms or a substituted or unsubstituted aryl group of 6 to 20 carbon atoms. Illustrative examples of the straight, branched or cyclic alkyl group include methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, and cyclohexylethyl. Illustrative examples of the substituted or unsubstituted aryl group include phenyl, methylphenyl, naphthyl, anthryl, phenanthryl, and pyrenyl. $R^4$ to $R^{13}$ are independently hydrogen or monovalent hydrocarbon groups of 1 to 15 carbon atoms which may contain a hetero atom, examples of which include straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted ones of these alkyl groups wherein some hydrogen atoms are replaced by hydroxyl, alkoxy, carboxy, alkoxycarbonyl, oxo, amino, alkylamino, cyano, mercapto, alkylthio, and sulfo groups. Any pair of R's selected from among $R^4$ to $R^{13}$ (for example, a pair of $R^4$ and $R^5$, $R^6$ and $R^8$, $R^6$ and $R^9$, $R^7$ and $R^9$, $R^7$ and $R^{13}$, $R^8$ and $R^{12}$, $R^{10}$ and $R^{11}$, and/or $R^{11}$ and $R^{12}$), taken together, may form a ring with the adjacent carbon atom(s). When these R's form a ring, they represent divalent hydrocarbon groups of 1 to 15 carbon atoms which may contain a hetero atom, which are exemplified by the above exemplary groups for the monovalent hydrocarbon groups, with one hydrogen atom eliminated. Alternatively, two of $R^4$ to $R^{13}$ which are attached to adjacent carbon atoms (for example, $R^4$ and $R^{13}$, $R^{10}$ and $R^{13}$, and $R^6$ and $R^8$) may directly (without any intervening atom) bond together to form a double bond.

$R^{14}$ is a straight, branched or cyclic alkyl group of 1 to 15 carbon atoms, for example, methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, but:ylcyclohexyl, adamantyl, ethyladamantyl, and butyladamantyl.

Illustrative, non-limiting examples of the ester compound according to the invention are given below.

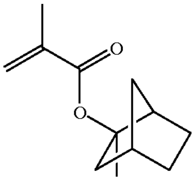
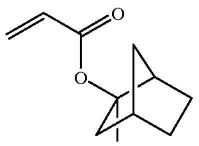

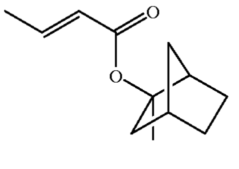
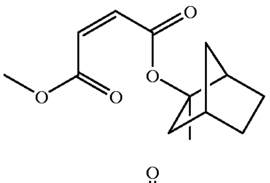

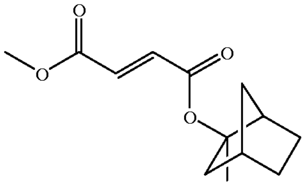
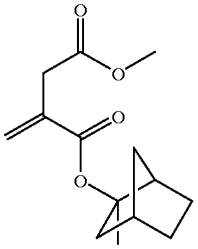

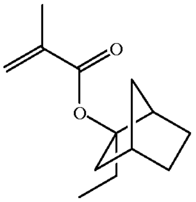
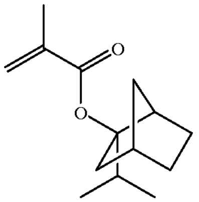

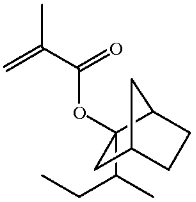
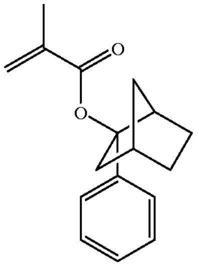

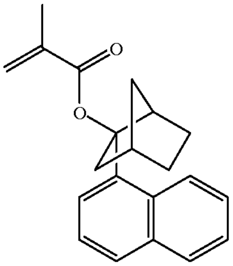
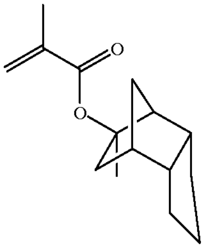

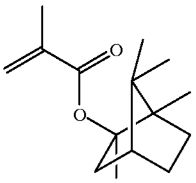
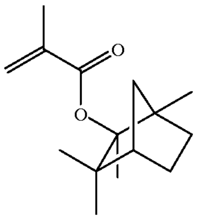

-continued

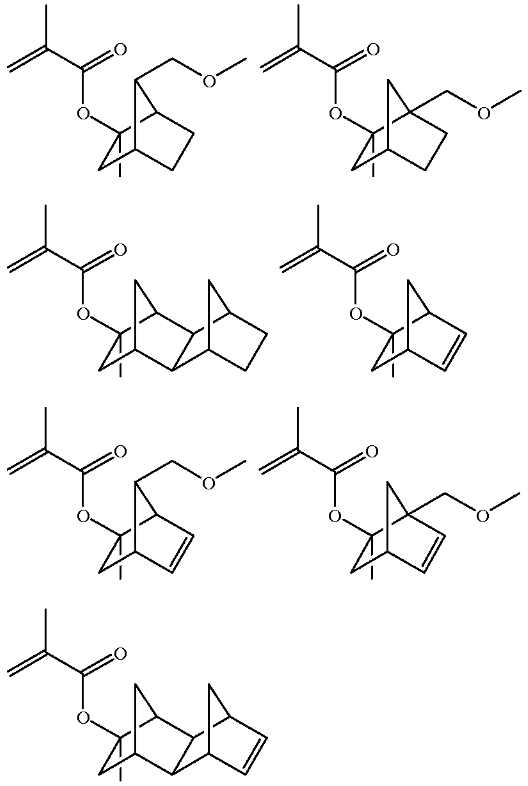

The ester compounds of the invention can be prepared, for example, by the following procedure although the invention is not limited thereto.

1st step

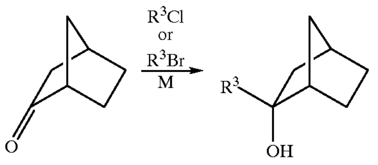

2nd step

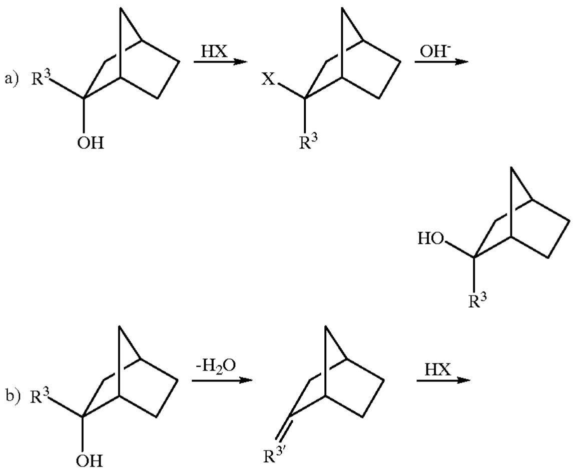

-continued

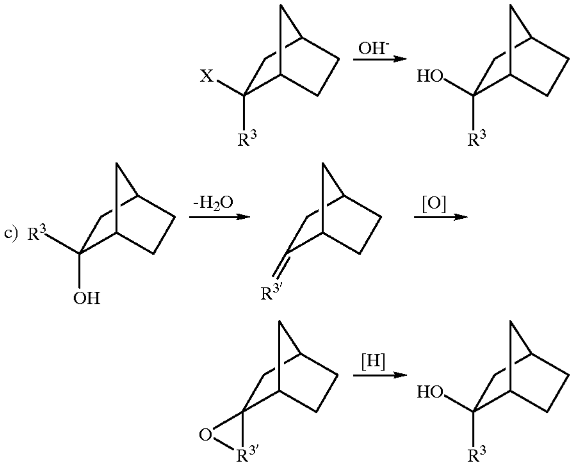

3rd step

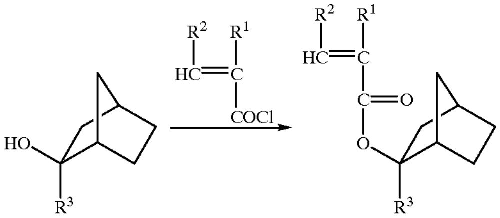

(1)

Herein, $R^1$ to $R^{13}$ are as defined above although $R^4$ to $R^{13}$ are omitted for the brevity of description. $R^{3'}$ is identical with $R^3$ except that one hydrogen atom is eliminated from the carbon at the bond position. M represents a metal, HX an acid, OH a base, [0] an oxidizing agent, and [H] a reducing agent.

The first step is to effect nucleophilic addition reaction to the carbonyl of a bicyclo[2.2.1]heptan-2-one or derivative thereof to convert it into an endo-form alcohol. Illustrative of this step are Grignard reaction and reaction using organic lithium compounds although the reaction involved in this step is not limited thereto. Reaction readily takes place under well-known conditions. Reaction is preferably carried out by mixing the reactants: a ketone compound and an alkyl halide or aryl halide with the metal M such as magnesium or lithium in a solvent such as tetrahydrofuran or diethyl ether and heating or cooling the reaction mixture if desired.

It is noted that only the endo-form alcohol yields from the first step and that the following isomerization step is essential to obtain an exo-form alcohol from which the end exo-form ester is produced.

The second step is to convert the endo-form alcohol from the first step into an exo-form alcohol. Some illustrative, non-limiting, procedures of the second step include (a) replacement reaction accompanied by stereo-inversion using acid HX, followed by alkali hydrolysis or decomposition in alkali-containing solvent; (b) dehydration, and addition of acid HX to the resulting olefin, followed by alkali hydrolysis or decomposition in alkali-containing solvent; and (c) dehydration and epoxidization of the resulting olefin, followed by reductive cleavage of epoxy. Reaction readily takes place under well-known conditions, with the detail conditions for the respective procedures being omitted. Illustrative, non-limiting examples of the acid HX include inorganic acids such as hydrochloric acid, aqueous hydrochloric acid, hydrobromic acid, hydroiodic acid, and sulfuric acid, and organic acids such as formic acid, acetic acid, propionic acid, benzoic acid, chloroformic acid, chloroacetic acid, dichloroacetic acid, trichloroacetic acid, fluoroacetic acid, difluoroacetic acid, trifluoroacetic acid, and 3,3,3-trifluoropropionic acid. Illustrative, non-limiting examples of the base $OH^-$ include inorganic hydroxides such as sodium hydroxide, lithium hydroxide, potassium hydroxide, and barium hydroxide, inorganic carbonates such as sodium carbonate, sodium hydrogen carbonate, lithium carbonate, and potassium carbonate, and alkoxides such as sodium methoxide, sodium ethoxide, lithium methoxide, lithium ethoxide, lithium tert-butoxide, and potassium tert-butoxide, and organic bases such as diethylamine, triethylamine, tri-n-butylamine and dimethylaniline. Illustrative, non-limiting examples of the oxidizing agent [0] include peracids such as performic acid, peracetic acid, trifluoroperacetic acid, and m-chloroperbenzoic acid, and peroxides such as hydrogen peroxide, dimethyl dioxirane, and tert-butyl hydroperoxide. It is noted that when reaction is effected using the oxtdizing agent, a metal salt may be co-present as a catalyst. Illustrative, non-limiting examples of the reducing agent [H] include metal hydrides such as boran, alkylboran, dialkylboran, dialkylsilane, trialkylsilane, sodium hydride, lithium hydride, potassium hydride, and calcium hydride; complex hydride salts such as lithium boron hydride, sodium boron hydride, calcium boron hydride, lithium aluminum hydride, and sodium aluminum hydride; alkoxy complex hydride salts such as lithium trimethoxyaluminum hydride, lithium diethoxyaluminum hydride, lithium tri-tert-butoxyaluminum hydride, RED-AL, and sodium trimethoxyborohydride; and alkyl complex hydride salts such as lithium triethylborohydride, K-Selectride, and L-Selectride.

The third step is to esterify the exo-form alcohol. Reaction readily takes place under well-known conditions. Reaction is preferably carried out by successively or simultaneously adding the reactants: the exo-form alcohol, a carboxylic acid halide (e.g., acrylic acid chloride or methacrylic acid chloride), and a base (e.g., triethyl-amine) in a solvent such as methylene chloride and cooling the reaction mixture if desired.

Polymer

In the second aspect, the invention provides a polymer or high molecular weight compound comprising units of the following general formula (1a) which are obtained using the ester compound of formula (1) as a monomer, and having a weight average molecular weight of 1,000 to 500,000, preferably 5,000 to 100,000.

(1a)

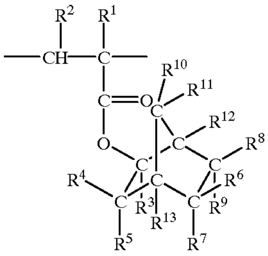

Herein, $R^1$ to $R^{13}$ are as defined above. The formula also represents an enantiomer.

The polymer of the invention may further comprise recurring units of at least one type selected from recurring units of the following general formulae (2a) to (13a) which are obtained using monomers, of the following general formulae (2) to (13).

(2)

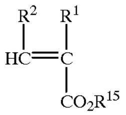

(3)

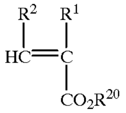

(4)

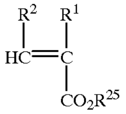

(5)

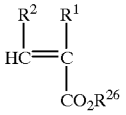

(6)

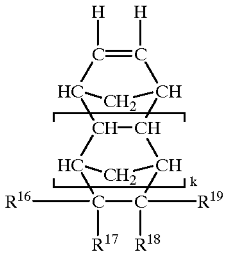

(7)

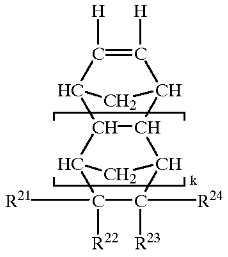

(8)

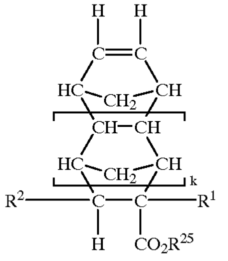

-continued
(9)
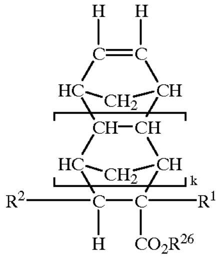
(10)
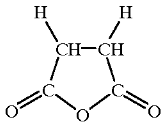
(11)
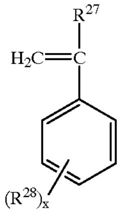
(12)
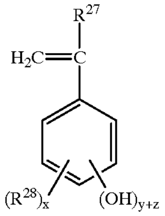
(13)
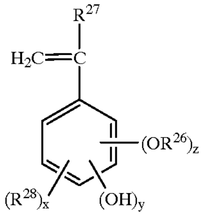
(2a)
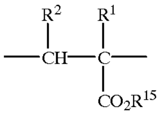
(3a)
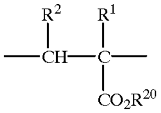
(4a)
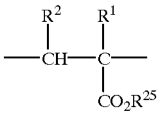
-continued
(5a)
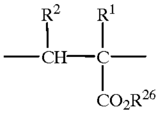
(6a)
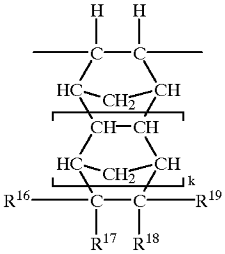
(7a)
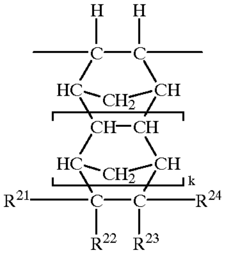
(8a)
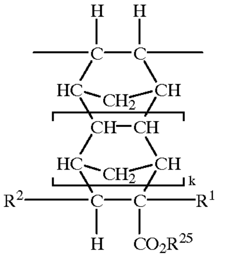
(9a)
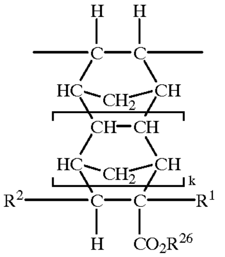
(10a)
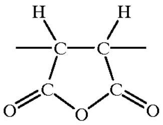
(11a)
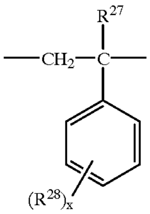

-continued (12a)

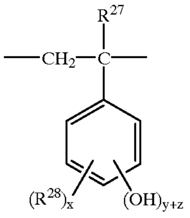

(13a)

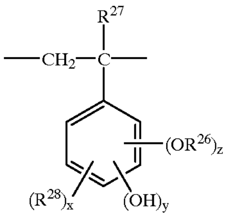

In the above formulae, k is equal to 0 or 1. Then formulae (6a) to (9a) may also be represented by the following formulae (6a-1) to (9a-2).

(6a-1)

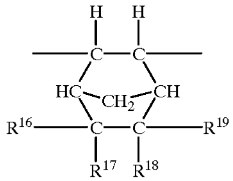

(7a-1)

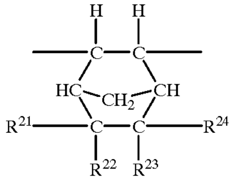

(8a-1)

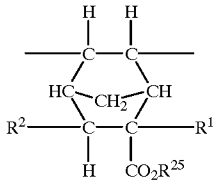

(9a-1)

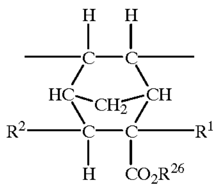

-continued (6a-2)

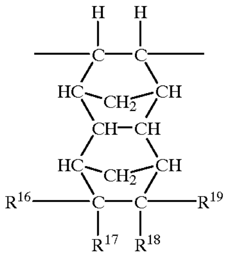

(7a-2)

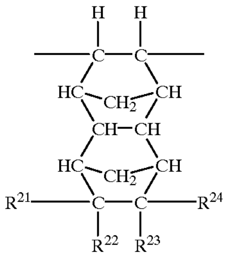

(8a-2)

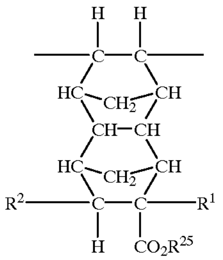

(9a-2)

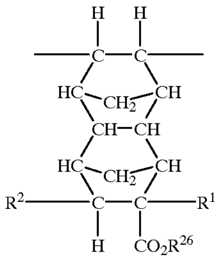

Herein, $R^1$ and $R^2$ are as defined above. $R^{15}$ is hydrogen or a monovalent hydrocarbon group of 1 to 15 carbon atoms having a carboxyl or hydroxyl group, for example, carboxyethyl, carboxybutyl, carboxycyclopentyl, carboxycyclohexyl, carboxynorbornyl, carboxyadamantyl, hydroxyethyl, hydroxybutyl, hydroxycyclopentyl, hydroxycyclohexyl, hydroxynorbornyl, or hydroxyadamantyl. At least one of $R^{16}$ to $R^{19}$ is hydrogen or a monovalent hydrocarbon group of 1 to 15 carbon atoms having a carboxyl or hydroxyl group, while the remaining R's are independently hydrogesn or straight, branched or cyclic alkyl groups of 1 to 15 carbon atoms. Examples of the carboxyl or hydroxyl-bearing monovalent hydrocarbon group of 1 to 15 carbon atoms include carboxy, carboxymethyl, carboxyethyl, carboxybutyl, hydroxymethyl, hydroxyethyl, hydroxybutyl, 2-carboxyethoxycarbonyl, 4-carboxybutoxycarbonyl, 2-hydroxyethoxycarbonyl, 4-hydroxybutoxycarbonyl, carboxycyclopentyloxycarbonyl, carboxycyclohexyloxycarbonyl, carboxynorbornyloxycarbonyl, carboxyadamantyloxycarbonyl, hydroxycyclopentyloxycarbonyl, hydroxycyclohexyloxycarbonyl, hydroxynorbornyloxycarbonyl, and hydroxyadamantyloxycarbonyl. Examples of the straight, branched or cyclic alkyl group of 1 to 15 carbon atoms are the same as exemplified for $R^{14}$. $R^{16}$ to $R^{19}$, taken together, may form a ring, and in that event, at least one of $R^{16}$ to $R^{19}$ is a divalent hydrocarbon group of 1 to 15 carbon atoms having a carboxyl or hydroxyl group, while the remaining R's are independently straight, branched or cyclic alkylene groups of 1 to 15 carbon atoms. Examples of the carboxyl or hydroxyl-bearing divalent hydrocarbon group of 1 to 15 carbon atoms include the groups exemplified as the carboxyl or hydroxyl-bearing monovalent hydrocarbon group, with one hydrogen atom eliminated therefrom. Examples of the straight, branched or cyclic alkylene groups of 1 to 15 carbon atoms include the groups exemplified for $R^{14}$, with one hydrogen atom eliminated therefrom.

$R^{20}$ is a monovalent hydrocarbon group of 3 to 15 carbon atoms containing a —$CO_2$— partial structure, for example, 2-oxooxolan-3-yl, 4,4-dimethyl-2-oxooxolan-3-yl, 4-methyl-2-oxooxan-4-yl, 2-oxo-1,3-dioxolan-4-ylmsthyl, and 5-methyl-2-oxooxolan-5-yl. At least one of $R^{21}$ to $R^{24}$ is a monovalent hydrocarbon group of 2 to 15 carbon atoms containing a —$CO_2$— partial structure, while the remaining R's are independently hydrogen or straight, branched or cyclic alkyl groups of 1 to 15 carbon atoms. Examples of the monovalent hydrocarbon group of 2 to 15 carbon atoms containing a —$CO_2$— partial structure include 2-oxooxolan-3-yloxycarbonyl, 4,4-dimethyl-2-oxooxolan-3-yloxycarbonyl, 4-methyl-2-oxooxan-4-yloxycarbonyl, 2-oxo-1,3-dioxolan-4-ylmethyloxycarbonyl, and 5-methyl-2-oxooxolan-5-yloxycarbonyl. Examples of the straight, branched or cyclic alkyl groups of 1 to 15 carbon atoms are the same as exemplified for $R^{14}$. $R^{21}$ to $R^{24}$, taken together, may form a ring, and in that event, at least one of $R^{21}$ to $R^{24}$ is a divalent hydrocarbon group of 1 to 15 carbon atoms containing a —$CO_2$— partial structure, while the remaining R's are independently straight, branched or cyclic alkylene groups of 1 to 15 carbon atoms. Examples of the divalent hydrocarbon group of 1 to 15 carbon atoms containing a —$CO_2$— partial structure include 1-oxo-2-oxapropane-1,3-diyl, 1,3-dioxo-2-oxapropane-1,3-diyl, 1-oxo-2-oxabutane-1,4-diyl, and 1,3-dioxo-2-oxabutane-1,4-diyl, as well as the groups exemplified as the monovalent hydrocarbon group containing a —$CO_2$— partial structure, with one hydrogen atom eliminated therefrom. Examples of the straight, branched or cyclic alkylene groups of 1to 15 carbon atoms include the groups exemplified for $R^{14}$, with one hydrogen atom eliminated therefrom.

$R^{25}$ is a polycyclic hydrocarbon group having 7 to 15 carbon atoms or an alkyl group containing a polycyclic hydrocarbon group, for example, norbornyl, bicyclo[3.3.1]-nonyl, tricyclo[5.2.1.$0^{2,6}$]decyl, adamantyl, ethyladamantyl, butyladamantyl, norbornylmethyl, and adamantylmethyl. $R^{26}$ is an acid labile group. $R^{27}$ is hydrogen or methyl. $R^{28}$ is a straight, branched or cyclic alkyl group of 1 to 8 carbon atoms, examples of which are as exemplified for $R^3$. The letter k is equal to 0 or 1, and x, y and z are integers of 0 to 3, preferably 0 to 2, satisfying $x+y+z \leqq 5$, preferably $x+y+z \leqq 3$, and $1 \leqq y+z$.

Illustrative groups of the acid labile group represented by $R^{26}$ include groups of the following formulae (14) and (15), tertiary alkyl groups of 4 to 20 carbon atoms, preferably 4 to 15 carbon atoms, trialkylsilyl groups whose alkyls each have 1 to 6 carbon atoms, and oxoalkyl groups of 4 to 20 carbon atoms.

(14)

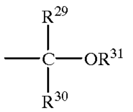

(15)

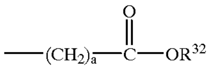

Herein, $R^{29}$ and $R^{30}$ each are hydrogen or a straight, branched or cyclic alkyl group of 1 to 18 carbon atoms, preferably 1 to 10 carbon atoms, for example, methyl, ethyl, propyl, isopropyl, n-butyl, sec-butyl, tert-butyl, cyclopentyl, cyclohexyl, 2-ethylhexyl, and n-octyl. $R^{31}$ is a monovalent hydrocarbon group of 1 to 18 carbon atoms, preferably 1 to 10 carbon atoms, which may have a hetero atom such as an oxygen atom, for example, straight, branched or cyclic alkyl groups, in which some hydrogen atoms are replaced by hydroxyl, alkoxy, oxo, amino, or alkylamino groups. More illustrative of the $R^{31}$ group are the substituted alkyl groups shown below.

$—(CH_2)_4—OH$ $—(CH_2)_2—O—(CH_2)_3—CH_3$

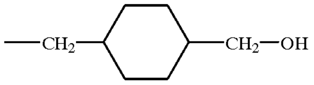

$—(CH_2)_2—O—(CH_2)_2—OH$ $—(CH_2)_6—OH$

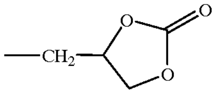

A pair of $R^{29}$ ad $R^{30}$ $R^{29}$ and $R^{31}$, or $R^{30}$ and $R^{31}$, taken together, may form a ring. $R^{29}$, $R^{30}$ and $R^{31}$ each represent straight or branched alkylene groups of 1 to 18 carbon atoms, preferably 1 to 10 carbon atoms when they form a ring.

$R^{32}$ is a tertiary alkyl group of 4 to 20 carbon atoms, preferably 4 to 15 carbon atoms, trialkylsilyl group whose alkyls each have 1 to 6 carbon atoms, oxoalkyl group of 4 to 20 carbon atoms, or group of above formula (14). Letter a is an integer of 0 to 6.

Exemplary tertiary alkyl groups include tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl. Exemplary trialkylsilyl groups are those whose alkyl groups each have 1 -to 6 carbon atoms, such as trimethylsilyl, triethylsilyl and dimethyl-tert-butylsilyl. Examples of oxoalkyl groups include 3 -oxocyclohexyl, 2-oxooxan-4-yl, and 4-methyl-2-oxooxolan-4-yl.

Of the acid labile groups of formula (14), straight: and branched groups are illustrated below.

$—CH_2—O—CH_3$ $—CH_2—O—CH_2—CH_3$

-continued

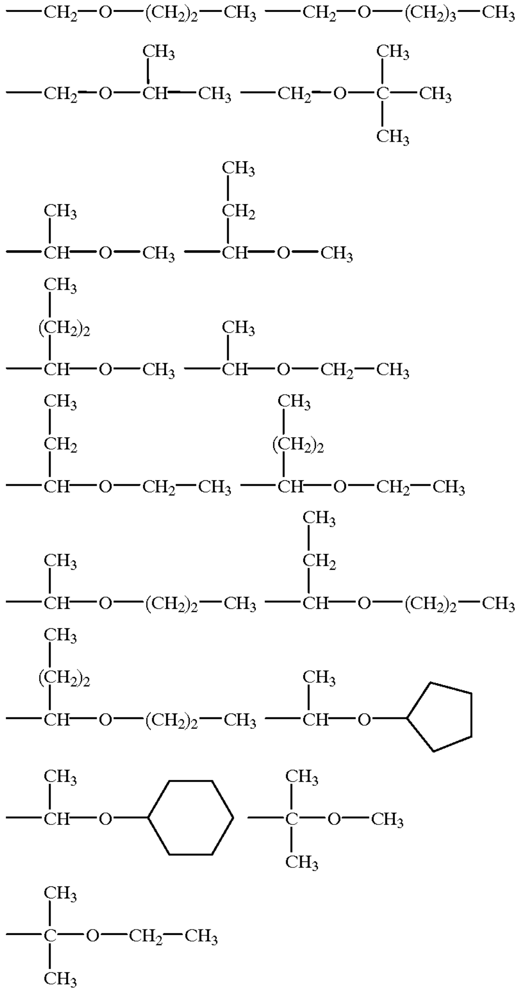

Of the acid labile groups of formula (14), cyclic groups are illustrated below.

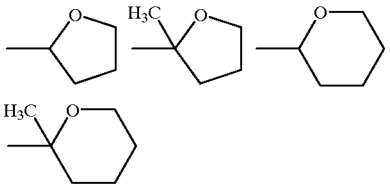

Illustrative examples of the acid labile group of formula (15) include tert-butoxycarbonyl, tert-butoxycarbonylmethyl, tert-amyloxycarbonyl, tert-amyloxycarbonyl-methyl, 1,1-diethylpropyloxycarbonyl, 1,1-diethylpropyloxy-carbonylmethyl, 1-ethylcyclopentyloxycarbonyl, 1-ethylcyclopentyloxycarbonylmethyl, 1-ethyl-2-cyclopentenyloxy-carbonyl, 1-ethyl-2-cyclopentenyloxycarbonylmethyl, 1-ethoxyethoxycarbonylmethyl, 2-tetrahydropyranyloxycarbonyl-methyl, and 2-tetrahydrofuranyloxycarbonylmethyl.

The polymer of the invention may be prepared by polymerizing an ester compound of formula (1) or by copolymerizing a first monomer in the form of an ester compound of formula (1) with a second monomer in the form of at least one compound of formulae (2) to (13). By properly adjusting the proportion of the respective monomers used in the copolymerization reaction, the polymer can be tailored so that it may exert the preferred performance when blended in resist compositions.

In addition to (i) the monomer of formula (1) and (ii) the monomer or monomers of formulae (2) to (13), the polymer of the invention may have copolymerized therewith (iii) another monomer having a carbon-to-carbon double bond other than (i) and (ii). Examples of the additional monomer (iii) include substituted acrylic acid esters such as methyl methacrylate, methyl crotonate, dimethyl maleate, and dimethyl itaconate, unsaturated carboxylic acids such as maleic acid, fumaric acid and itaconic acid, substituted or unsubstituted norbornenes such as norbornene and methyl norbornene-5-carboxylate, and unsaturated acid anhydrides such as itaconic anhydride.

The polymers of the invention may contain (I) more than 0 mol % to 100 mol % preferably 20 to 90 mol %, more preferably 30 to 80 mol % of units of formula (1a) derived from the monomer of formula (1), (II) 0 mol % to less than 100 mol % preferably 1 to 95 mol %, more preferably 5 to 90 mol % of units of one or more types of formulae (2a) to (13a) derived from the monomers of formulae (2) to (13), and optionally, (III) 0 to 80 mol %, preferably 0 to 70 mol %, more preferably 0 to 50 mol % of units of one or more types derived from the additional monomers (iii).

The polymers of the invention have a weight average molecular weight of 1,000 to 500,000, preferably 3,000 to 100,000. Outside the range, the etching resistance may become extremely low and the resolution may become low because a substantial difference in rate of dissolution before and after exposure is lost.

In the method according to the third aspect of the invention, a polymer is prepared by effecting radical polymerization, anionic polymerization or coordination polymerization between an ester compound of formula (1) and another compound having a carbon-to-carbon double bond, which is typically selected from the above-described monomers (ii) and (iii).

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about ½ hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about ½ hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about ½ hour to about 48 hours. Reaction conditions outside the described range may be employed if desired.

Resist Composition

Since the polymer of the invention is useful as the base polymer of a resist composition, the other aspect of the invention provides a resist composition comprising the polymer. Specifically, the resist composition is defined as comprising the polymer, a photoacid generator, and an organic solvent.

Photoacid Generator

The photoacid generator is a compound capable of generating an acid upon exposure to high energy radiation or electron beams and includes the following:

(i) onium salts of the formula (P1a-1), (P1a-2) or (Plb),
(ii) diazomethane derivatives of the formula (P2),
(iii) glyoxime derivatives of the formula (P3),
(iv) bissulfone derivatives of the formula (P4),
(v) sulfonic acid esters of N-hydroxyimide compounds of the formula (P5),
(vi) β-ketosulfonic acid derivatives,
(vii) disulfone derivatives,
(viii) nitrobenzylsulfonate derivatives, and
(ix) sulfonate derivatives.

These photoacid generators are described in detail.

(i) Onium salts of formula (P1a-1), (P1a-2) or (P1b):

P1a-1

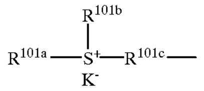

P1a-2

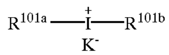

Herein, $R^{101a}$, $R^{101b}$, and $R^{101c}$ independently represent straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. $K^-$ is a non-nucleophilic counter ion.

$R^{101a}$, $R^{101b}$, and $R^{101c}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methyl-cyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by $K^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, bennzenesulfonate, 4-fluorobenzenesulfonate, and 1,2,3,4,5-pentafluorobenzenesulfonate, and alkylsulfonate ions such as mesylate and butanesulfonate.

P1b

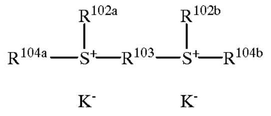

Herein, $R^{102a}$ and $R^{102b}$ independently represent straight, branched or cyclic alkyl groups of 1 to 8 carbon atoms. $R^{103}$ represents a straight, branched or cyclic alkylene groups of 1 to 10 carbon atoms. $R^{104a}$ and $R^{104b}$ independently represent 2-oxoalkyl groups of 3 to 7 carbon atoms. $K^-$ is a non-nucleophilic counter ion.

Illustrative of the groups represented by $R^{102a}$ a and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl. Illustrative examples of the counter ion represented by $K^-$ are the same as exemplified for formulae (P1a-1) and (P1a-2).

(ii) Diazomethane derivatives of formula (P2)

P2

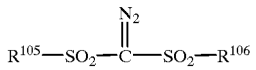

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tertbutoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime derivatives of formula (P3)

P3

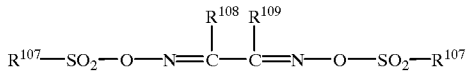

Herein, $R^{107}$, $R^{108}$, and $R^{109}$ indepencdently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone derivatives of formula (P4)

P4

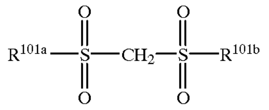

Herein, $R^{101a}$ and $R^{101b}$ are as defined above.

(v) Sulfonic acid esters of N-hydroxyimide compounds of formula (P5)

P5

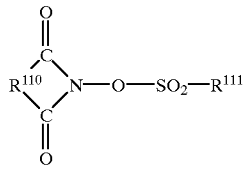

Herein, $R^{110}$ is an arylene group o:f 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, 1,2-ethylene, 1,3-propylene, 1,4-butylene, 1-phenyl-1,2-ethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; the alkoxy groups of 1 to 4 carbon atoms include methoxy, ethoxy, propoxy, isopropoxy, n-butoxy, isobutoxy, and tert-butoxy; the phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl; the hetero-aromatic groups of 3 to 5 carbon atoms include pyridyl and furyl.

Illustrative examples of the photoacid generator include:

onium salts such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclo-hexyl)sulfonium trifluoromethanesulfonate, ethylenebis-[methyl(2-oxocyclopentyl)sulfonium trifluoromethanesulfonate], and 1,2'-naphthylcarbonylmethyltetrahydrothiophenium triflate;

diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)(diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1- cyclohexylsulfonyl-1-(tert-butylsulfonyl)diazomethane, 1-cyclohexylsulfonyl-1 -(tert-amylsulfonyl)diazomethane, and 1-tert-amylsulfonyl-1-(tert-butylsulfonyl)diazomethane;

glyoxime derivatives such as bis-o-(p-toluene-sulfonyl)-α-dimethylglyoxime, bis-o-(p-toluenesulfonyl)-α-diphenylglyoxime, bis-o-(p-toluenesulfonyl)-α-dicyclohexyl- glyoxime, bis-o-(p-toluenesulfonyl)-2,3-pentanedione-glyoxime, bis-o-(p-toluenesulfonyl)-2-methyl-3,4-pentanedioneglyoxime, bis-o-(n-butanesulfonyl) -α-dimethylglyoxime, bis-o-(n-butanesulfonyl)-α-diphenylglyoxime, bis-o-(n-butanesulfonyl)-α-dicyclohexylglyoxime, bis-o-(n-butanesulfonyl)-2,3-pentanedioneglyoxime, bis-o-(n-butanesulfonyl)-2-methyl-3,4-pentanedioneglyoxime, bis-o-(methanesulfonyl)-α-dimethylglyoxime, bis-o-(trifluoromethanesulfonyl)-α-dimethylglyoxime, bis-o-(1,1,1-trifluoroethanesulfonyl)-α-dimethylglyoxime, bis-o-(tert-butanesulfonyl)-α-dimethylglyoxime, bis-o-(perfluorooctanesulfonyl)-α-dimethylglyoxime, bis-o-(cyclohexane-sulfonyl)-α-dimethylglyoxime, bis-o-(benzenesulfonyl)-α-dimethylglyoxime, bis-o-(p-fluorobenzenesulfonyl)-α-dimethylglyoxime, bis-o-(p-tert-butylbenzenesulfonyl)-α-dimethylglyoxime, bis-o-(xylenesulfonyl)-α-dimethylglyoxime, and bis-o-(camphorsulfonyl)-α-dimethylglyoxime;

bissulfone derivatives such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane;

β-ketosulfone derivatives such as 2-cyclohexyl-carbonyl-2-(p-toluenesulfonyl)propane and 2-isopropyl-carbonyl-2-(p-toluenesulfonyl)propane;

disulfone derivatives such as diphenyl disulfone and dicyclohexyl disulfone;

nitrobenzyl sulfonate derivatives such as 2,6-dinitrobenzyl p-toluenesulfonate and 2,.4-dinitrobenzyl p-toluenesulfonate;

sulfonic acid ester derivatives such as 1,2,3-tris(methanesulfonyloxy)benzene, 1,2,3-tris(trifluoromethanesulfonyloxy)benzene, and 1,2,3-tris(p-toluene-sulfonyloxy)benzene; and sulfonic acid esters of N-hydroxyimides such as N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p)-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethylbenzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethanesulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxyimide methanesulfonate, N-hydroxy-5-norbornene-2,3-dicarboxyimide trifluoromethanesulfonate, and N-hydroxy-5-norbornene-2,3-dicarboxyimide p-toluenesulfonate.

Preferred among these photoacid generators are onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocylohexyl)sulfonium trifluoromethanesulfonate, and 1,2'-naphthylcarbonylmethyltetrahydrothiophenium triflate; diazomethane derivatives such as bis(benzenesulfonyl) diazomethane, bis(p-toluenesulfonyl)diazomethane, bis (cyclohexylsulfonyl)diazomethane, bis(n-butylsulfonyl) diazomethane, bis(isobutylsulfonyl)diazomethane, bis (secbutylsulfonyl)diazomethane, bis(n-propylsulfonyl) diazomethane, bis(isopropylsulfonyl)diazomethane, and bis (tert-butylsulfonyl)diazomethane; glyoxime derivatives such as bis-o-(p-toluenesulfonyl)-α-dimethylglyoxime and bis-o-(n-butanesulfonyl)-α-dimethylglyoxime; bissulfone derivatives such as bisnaphthylsulfonylmethane; and sulfonic acid esters of N-hydroxyimide compounds such as N-hydroxysuccinimide methanesulfonate, N-hydroxysuccinimide trifluoromethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide p-toluenesulfonate, N-hydroxynaphthalimide methanesulfonate, and N-hydroxynaphthalimide benzenesulfonate.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.1 to 15 parts, and especially 0.5 to 8 parts by weight, per 100 parts by weight of the base resin (all parts are by weight, hereinafter). Less than 0.1 part of the photoacid generator would provide a poor sensitivity whereas more than 15 parts of the photoacid generator would lower the rate of alkali dissolution to reduce the resolution of resist compositions and also lower the heat resistance because of the excessive presence of lower molecular weight components.

Organic Solvent

The organic solvent used herein may be any organic solvent in which the base resin, photoacid generator, and other components are soluble. Illustrative, non-limiting, examples of the organic solvent include ketones such as cyclohexanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. These solvents may be used alone or in combinations of two or more thereof. Of the above organic solvents, it is recommended to use diethylene glycol dimethyl ether and 1-ethoxy-2-propanol because the photoacid generator serving as one of the resist components is most soluble therein, propylene glycol monomethyl ether acetate because it is a safe solvent, or a mixture thereof.

An appropriate amount of the organic solvent used is about 200 to 1,000 parts, especially about 400 to 800 parts by weight per 100 parts by weight of the base resin.

To the resist composition of the invention, another polymer other than the polymer of the invention may also be added. The other polymers that can be added to the resist composition are, for example, those polymers comprising units of the following formula (R1) or (R2) and having a weight average molecular weight of about 1,000 to about 500,000, especially about 5,000 to about 100,000 although the other polymers are not limited thereto.

(R1)

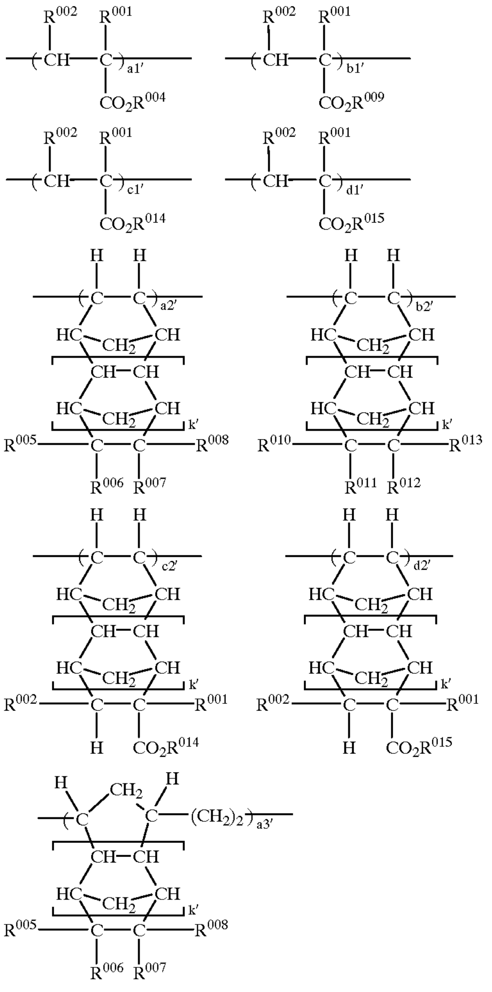

-continued

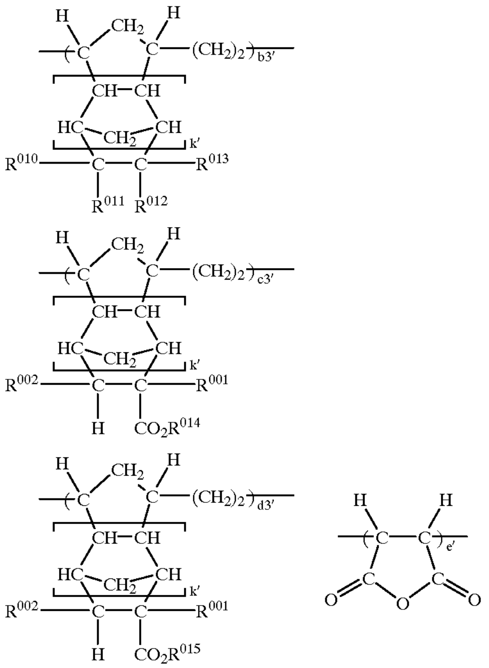

(R2)

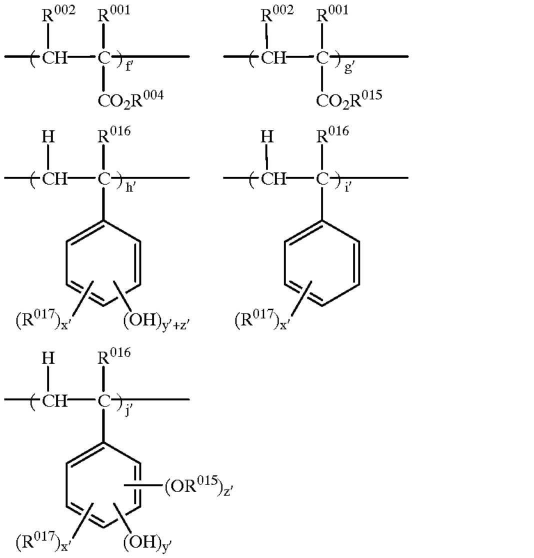

Herein, $R^{001}$ is hydrogen, methyl or $CH_2CO_2R^{003}$. $R^{002}$ is hydrogen, methyl or $CO_2R^{003}$. $R^{003}$ is a straight, branched or cyclic alkyl group of 1 to 15 carbon atoms. $R^{004}$ is hydrogen or a monovalent hydrocarbon group of 1 to 15 carbon atoms having a carboxyl or hydroxyl group. At least one of $R^{005}$ to $R^{008}$ represents a monovalent hydrocarbon group of 1 to 15 carbon atoms having a carboxyl or hydroxyl group while the remaining R's independently represent hydrogen or a straight, branched or cyclic alkyl group of 1 to 15 carbon atoms. Alternatively, $R^{005}$ to $R^{008}$, taken together, may form a ring, and in that event, at least one of $R^{005}$ to $R^{008}$ is a divalent hydrocarbon group of 1 to 15 carbon atoms having a carboxyl or hydroxyl group, while the remaining R's are independently straight, branched or cyclic alkylene groups of 1 to 15 carbon atoms. $R^{009}$ is a monovalent hydrocarbon group of 3 to 15 carbon atoms containing a —$CO_2$— partial structure. At least one of $R^{010}$ to $R^{013}$ is a monovalent hydrocarbon group of 2 to 15 carbon atoms containing a —$CO_2$— partial structure, while the remaining R's are independently hydrogen or straight, branched or cyclic alkyl groups of 1 to 15 carbon atoms. $R^{010}$ to $R^{013}$, taken together, may form a ring, and in that event, at least one of $R^{010}$ to $R^{013}$ is a divalent hydrocarbon group of 1 to 15 carbon atoms containing a —$CO_2$— partial structure, while the remaining R's are independently straight, branched or cyclic alkylene groups of 1 to 15 carbon atoms. $R^{014}$ is a polycyclic hydrocarbon group having 7 to 15 carbon atoms or an alkyl group containing a polycyclic hydrocarbon group. $R^{015}$ is an acid labile group. $R^{016}$ is hydrogen or methyl. $R^{017}$ is a straight, branched or cyclic alkyl group of 1 to 8 carbon atoms. Letter k' is (equal to 0 or 1; a1', a2', a3', b1', b2', b3', c1', c2', c3', d1', d2', d3', and e' are numbers from 0 to less than 1, satisfying a1'+a2'+a3'+b1'+b2'+b3'+c1'+c2'+c3'+d1'+d2'+d3'+e'=1; f', g', h', i', and j' are numbers from 0 to less than 1, satisfying f'+g'+h'+i'+j'=1. Illustrative examples of the respective groups are the same as exemplified for $R^1$ to $R^{28}$.

The inventive polymer and the other polymer are preferably blended in a weight ratio from 10:90 to 90:10, more preferably from 20:80 to 80:20. If the blend ratio of the inventive polymer is below this range, the resist composition would become poor in some of the desired properties. The properties of the resist composition can be adjusted by properly changing the blend ratio of the inventive polymer.

The polymer is not limited to one type and a mixture of two or more other polymers may be added. The use of plural polymers allows for easy adjustment of resist properties.

Dissolution Inhibitor

To the resist composition, a dissolution inhibitor may be added. The dissolution inhibitor is a compound having on the molecule at least two phenolic hydroxyl groups, in which an average of from 0 to 100 mol % of all the hydrogen atoms on the phenolic hydroxyl groups are replaced with acid labile groups or a compound having on the molecule at least one carboxyl group, in which an average of 80 to 100 mol % of all the hydrogen atoms on the carboxyl groups are replaced with acid labile groups, both the compounds having an average molecular weight within a range of 100 to 1,000, and preferably 150 to 800.

The degree of substitution of the hydrogen atoms on the phenolic hydroxyl groups or carboxyl groups with acid labile groups is on average at least 0 mol %, and preferably at least 30 mol %, of all the phenolic hydroxyl groups or carboxyl groups. The upper limit is 100 mol %, and preferably 80 mol %.

Preferable examples of such compounds having two or more phenolic hydroxyl groups or compounds having a carboxyl group include those of formulas (D1) to (D14) below.

D1

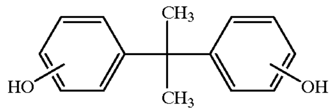

-continued

D2

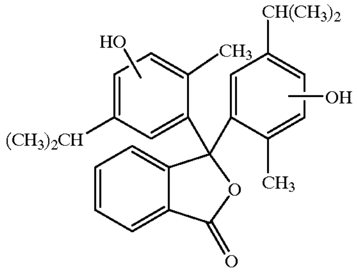

D3

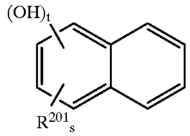

D4

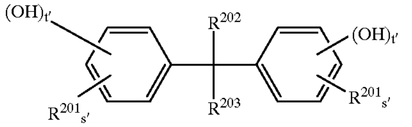

D5

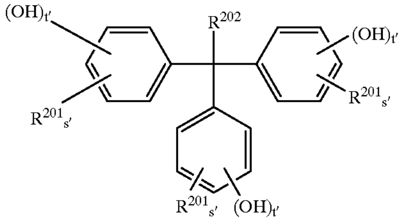

D6

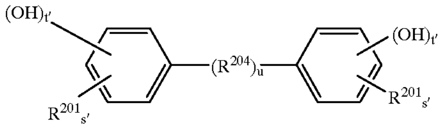

D7

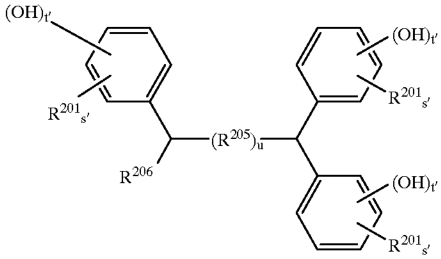

D8

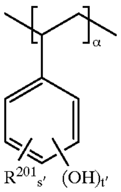

D9

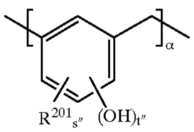

-continued

D10

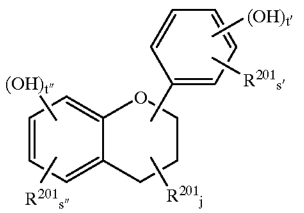

D11

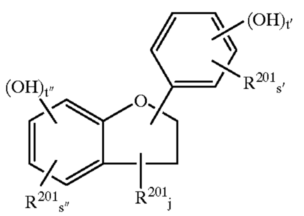

D12

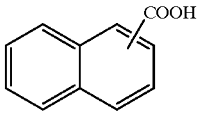

D13

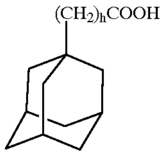

D14

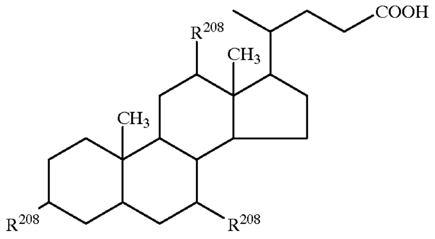

In these formulas, $R^{201}$ and $R^{202}$ are. each hydrogen or a straight or branched alkyl or alkenyl of 1 to 8 carbon atoms; $R^{203}$ is hydrogen, a straight or branched alkyl or alkenyl of 1 to 8 carbon atoms, or $-(R^{207})_h-COOH$; $R^{204}$ is $-(CH_2)_i-$(where i=2 to 10), an arylene of 6 to 10 carbon atoms, carbonyl, sulfonyl, an oxygen atom, or a sulfur atom; $R^{205}$ is an alkylene of 1 to 10 carbon atoms, an arylene of 6 to 10 carbon atoms, carbonyl, sulfonyl, an oxygen atom, or a sulfur atom; $R^{206}$ is hydrogen, a straight or branched alkyl or alkenyl of 1 to 8 carbon atoms, or a hydroxyl-substituted phenyl or naphthyl; $R^{207}$ is a straight or branched alkylene of 1 to 10 carbon atoms; $R^{208}$ is hydrogen or hydroxyl; the letter j is an integer from 0 to 5; u and h are each 0 or 1; s, t, s', t', s", and t" are each numbers which satisfy s+t=8, s'+t'=5, and s"+t" =4, and are such that each phenyl skeleton has at least one hydroxyl group; and $\alpha$ is a number such that the molecular weight of the compounds of formula (D8) or (D9) is from 100 to 1,000.

In the above formulas, suitable examples of $R^{201}$ and $R^{202}$ include hydrogen, methyl, ethyl, butyl., propyl, ethynyl, and cyclohexyl; suitable examples of $R^{203}$ include the same groups as for $R^{201}$ and $R^{202}$, as well as —COOH and $-CH_2COOH$; suitable examples of $R^{204}$ include ethylene, phenylene, carbonyl, sulfonyl, oxygen, and sulfur, suitable examples of $R^{205}$ include methylene as well as the same groups as for $R^{204}$; and suitable examples of $R^{206}$ include hydrogen, methyl, ethyl, butyl, propyl, ethynyl, cyclohexcyl, and hydroxyl-substituted phenyl or naphthyl.

Exemplary acid labile groups on the dissolution inhibitor include groups of the following general formula (14) or (15), tertiary alkyl groups of 4 to 20 carbon atoms, trialkylsilyl groups in which each of the alkyls has 1 to 6 carbon atoms, and oxoalkyl groups of 4 to 20 carbon atoms.

(14)

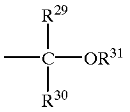

(15)

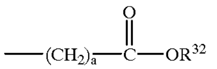

In these formulas, $R^{29}$ and $R^{30}$ are each hydrogen or a straight, branched or cyclic alkyl having 1 to 18 carbon atoms; and $R^{31}$ is a monovalent hydrocarbon group of 1 to 18 carbon atoms which may contain a heteroatom. A pair of $R^{29}$ and $R^{30}$, a pair of $R^{29}$ and $R^{31}$, or a pair of $R^{30}$ and $R^{31}$ may together form a ring, with the proviso that $R^{29}$, $R^{30}$, and $R^{31}$ are each a straight or branched alkylene of 1 to 18 carbon atoms when they form a ring. Also, $R^{32}$ is a tertiary alkyl group of 4 to 20 carbon atoms, a trialkysilyl group in which each of the alkyls has 1 to 6 carbon atoms, an oxoalkyl group of 4 to 20 carbon atoms,, or a group of the formula (14). The letter a is an integer from 0 to 6.

The dissolution inhibitor may be formulated in an amount of 0 to 50 parts, preferably 5 to 50 parts, and more preferably 10 to 30 parts, per 100 parts of the base resin, and may be used singly or as a mixture of two or more thereof. Less than 5 parts of the dissolution inhibitor may fail to yield an improved resolution, whereas the use of more than 50 parts would lead to thinning of the patterned film, and thus a decline in resolution.

The dissolution inhibitor can be synthesized by introducing acid labile groups into a compound having phenolic hydroxyl or carboxyl groups in accordance with an organic chemical formulation.

Basic Compound

In the resist composition of the invention, a basic compound may be blended. A suitable basic compound used herein is a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure, thus reducing substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropyl-amine, n-butylamine, iso-butylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylene-pentamine. Examples of suitable secondary aliphatic amines include dimethylamine, diethylamine, di-n-propylamine, di-iso-propylamine, di-n-butylamine, di-iso-butylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N, N-dimethyltetraethylenepentamine. Examples of suitable tertiary aliphatic amines include trimethylamine, triethylamine, tri-n-propylamine, tri-iso-propylamine, tri-n-butylamine, tri-iso-butylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenedliamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethyl[]aniline, 2-methylaniline, 3-methylaniline, 4-methylaniline, ethylaniline, propylaniline, trimethylaniline, 2 -nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and :N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamnine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxymethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formulas (B1) and (B2) may also be included.

B1

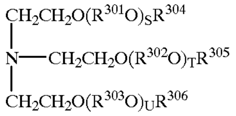

B2

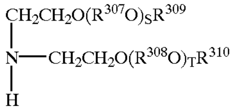

In the formulas, $R^{301}$, $R^{302}$, $R^{303}$, $R^{307}$ and $R^{308}$ are independently straight, branched or cyclic alkylenes of 1 to 20 carbon atoms; $R^{304}$, $R^{305}$, $R^{306}$, $R^{309}$ and $R^{310}$ are hydrogen, alkyls of 1 to 20 carbon atoms, or amino; $R^{304}$ and $R^{305}$, $R^{304}$ and $R^{306}$, $R^{305}$ and $R^{307}$, $R^{304}$ with $R^{305}$ and $R^{306}$ and $R^{309}$ and d $R^{310}$ may bond together to form rings; and S, T and U are each integers from 0 to 20, with the proviso that hydrogen is excluded from $R^{304}$, $R^{305}$, $R^{306}$, $R^{309}$ and $R^{310}$ when S, T and U are equal to 0.

The alkylene groups represented by $R^{301}{}_1$ $R^{302}$, $R^{303}$, $R^{307}$ and $R^{308}$ preferably have 1 to 20 carbon atoms, more preferably 1 to 10 carbon atoms, and most preferably 1 to 8 carbon atoms. Examples include methylene, ethylene, n-propylene, isopropylene, n-butylene, isobutylene, n-pentylene, isopentylene, hexylene, nonylene, decylene, cyclopentylene, and cyclohexylene.

The alkyl groups represented by $R^{304}$, $R^{305}$, $R^{306}$, $R^{309}$ and $R^{310}$ preferably have 1 to 20 carbon atoms, more preferably 1 to 8 carbon atoms, and most preferably 1 to 6 carbon atoms, and may be straight, branched or cyclic. Examples include methyl, ethyl, n-propyl, isopropyl, n-butyl, isobutyl, tert-butyl, n-pentyl, isopentyl, hexyl, nonyl, decyl, dodecyl, tridecyl, cyclopentyl, and cyclohexyl.

Where $R^{304}$ and $R^{305}$, $R^{304}$ and $R^{306}$, $R^{305}$ and $R^{306}$, $R^{304}$ with $R^{305}$ and $R^{306}$, and $R^{309}$ and $R^{310}$ form rings, the rings preferably have 1 to 20 carbon atoms, more preferably 1 to 8 carbon atoms, and most preferably 1 to 6 carbon atoms, and may have branching alkyl groups of 1 to 6 carbon atoms, and especially 1 to 4 carbon atoms.

S, T, and U are each integers from 0 to 20, preferably from 1 to 10, and more preferably from 1 to 8.

Illustrative examples of the compounds of formulas (B1) and (B2) include tris{2-(methoxymethoxy)ethyl}amine, tris{2-(methoxyethoxy)ethyl}amine, tris[2-{(2-methoxyethoxy)methoxy}ethyl]amine, tris{2-(2-methoxyethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8 5.5]eicosane, 1,4,10,13-tetraoxa-7,16-diazabicyclooctadecane, 1-aza-12-crown-4, 1-aza-15-crown-5, and 1-aza-18-crown-6. Especially preferred basic compounds are tertiary amines, aniline derivatives, pyrrolidine derivatives, pyridine derivatives, quinoline derivatives, amino acid derivatives, hydroxyl group-bearing nitrogenous compounds, hydroxyphenyl group-bearing nitrogenous compounds, alcoholic nitrogenous compounds, amide derivatives, imide derivatives, tris{2-(methoxymethoxy)ethyl}amine, tris{2-(2-methoxyethoxy)ethyl}amine, tris[2-{(2-methoxyethoxy)methyl}ethyl]amine, and 1-aza-15-crown-5.

The basic compound is preferably formulated in an amount of 0.001 to 10 parts, and especially 0.01 to 1 part, per part of the photoacid generator. Less than 0.001 part of the basic compound fails to achieve the desired effects thereof, while the use of more than 10 parts would result in too low a sensitivity and resolution.

Other Components

In the resist composition, a compound bearing a ≡C—COOH group in a molecule may be blended. Exemplary, non-limiting compounds bearing a ≡C—COOH group include one or more compounds selected from Groups I and II below. Including this compound improves the PED stability of the resist and ameliorates edge roughness on nitride film substrates. Group I:

Compounds in which some or all of the hydrogen atoms on the phenolic hydroxyl groups of the compounds of general formulas (A1) to (A10) below have been replaced with $—R^{401}—COOH$ (wherein $R^{401}$ is a straight or branched alkylene of 1 to 10 carbon atoms), and in which the molar ratio C/(C+D) of phenolic hydroxyl groups (C) to ≡C—COOH groups (D) in the molecule is from 0.1 to 1.0.

A1

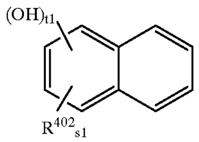

-continued

A2

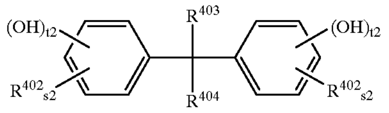

A3

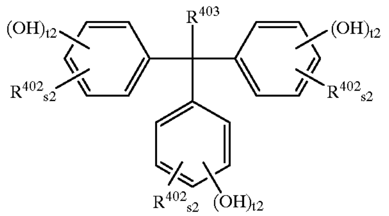

A4

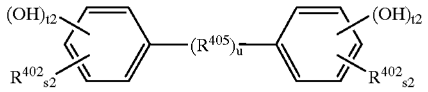

A5

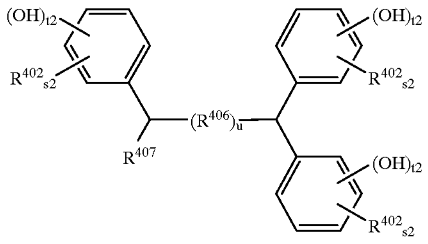

A6

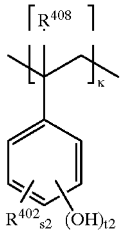

A7

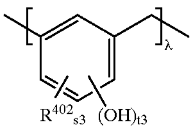

A8

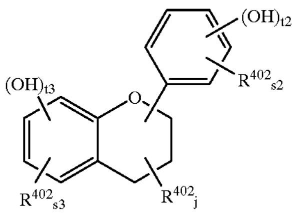

A9

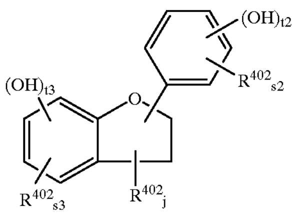

-continued

A10

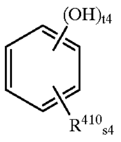

In these formulas, $R^{408}$ is hydrogen or methyl; $R^{402}$ and $R^{403}$ are each hydrogen or a straight or branched alkyl or alkenyl of 1 to 8 carbon atoms; $R^{404}$ is hydrogen, a straight or branched alkyl or alkenyl of 1 to 8 carbon atoms, or a $-(R^{409})_h-COOR'$ group (R' being hydrogen or $-R^{409}-COOH$); $R^{405}$ is $-(CH_2)_i-$(wherein i is 2 to 10), an arylene of 6 to 10 carbon atoms, carbonyl, sulfonyl, an oxygen atom, or a sulfur atom; $R^{406}$ is an alkylene of 1 to 10 carbon atoms, an arylene of 6 to 10 carbon atoms, carbooyl, sulfonyl, an oxygen atom, or a sulfur atom; $R^{407}$ is hydrogen, a straight or branched alkyl or alkenyl of 1 to 8 carbon atoms, or a hydroxyl-substituted phenyl or naphthyl.; $R^{409}$ is a straight or branched alkylene of 1 to 10 carbon atoms; $R^{410}$ is hydrogen, a straight or branched alkyl or alkenyl of 1 to 8 carbon atoms, or a $-R^{411}-COOH$ group; $R^{411}$ is a straight or branched alkylene of 1 to 10 carbon atoms; the letter j is an integer from 0 to 5; u and h are each 0 or 1; s1, t1, s2, t2, s3, t3, s4, and t4 are each numbers which satisfy s1+t1=8, s2+t2=5, s3+t3=4, and s4+t4=6, and are such that each phenyl skeleton has at least one hydroxyl group; κ is a number such that the compound of formula (A6) may have a weight average molecular weight of 1,000 to 5,000; and λ is a number such that the compound of formula (A7) may have a weight average molecular weight of 1,000 to 10,000.

Group II:

Compounds of general formulas (A11) to (A15) below.

A11

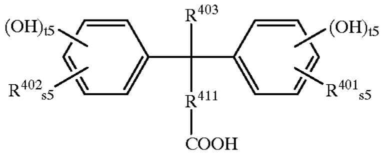

A12

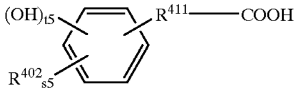

A13

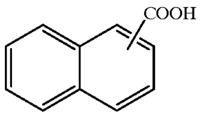

-continued

A14

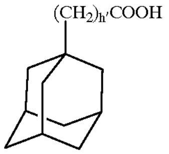

A15

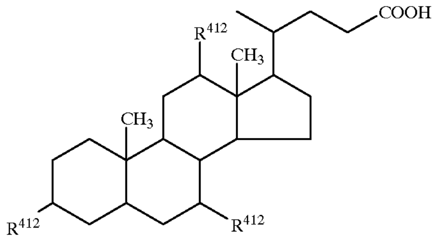

In these formulas, $R^{402}$, $R^{403}$, and $R^{411}$ are as defined above; $R^{412}$ is hydrogen or hydroxyl; s5 and t5 are numbers which satisfy s5≧0, t5≧0, and s5+t5=5; and h' is equal to 0 or 1.

Illustrative, non-limiting examples of the compound bearing a ≡C—COOH group include compounds of the general formulas AI-1 to AI-14 and AII-1 to AII-10 below.

AI-1

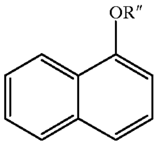

AI-2

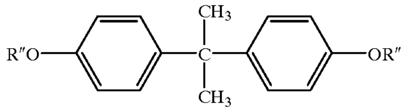

AI-3

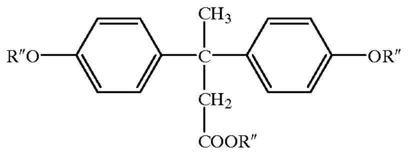

AI-4

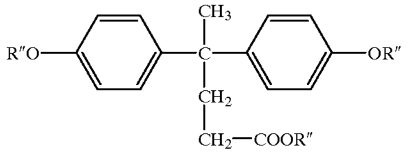

AI-5

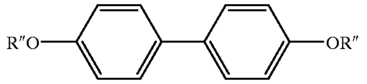

AI-6

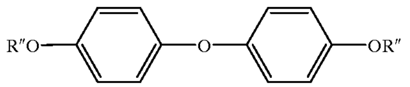

AI-7

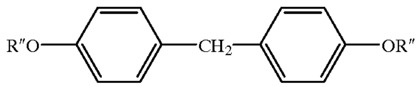

-continued
AI-8
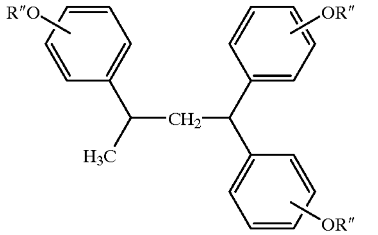
AI-9
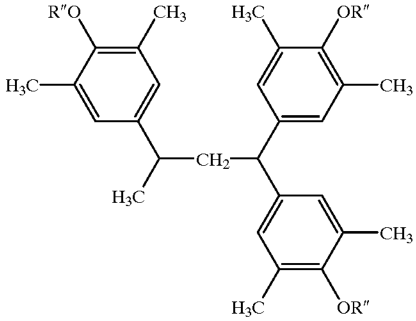
AI-10
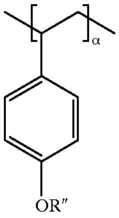
AI-11
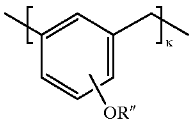
AI-12
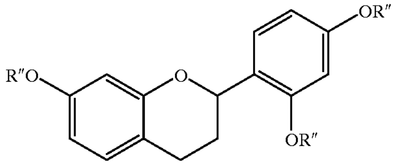
AI-13
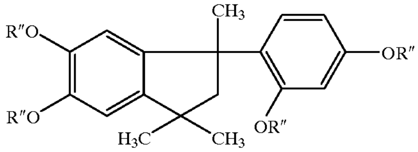
AI-14
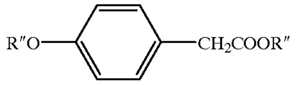
In the above formulas, R" is hydrogen or a $CH_2COOH$ group such that the $CH_2COOH$ group accounts for 10 to 100 mol % of R" in each compound, a and K are as defined above.
AII-1
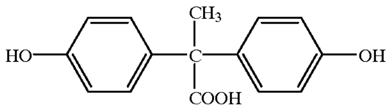
AII-2
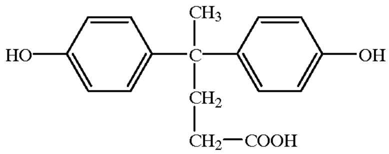
AII-3
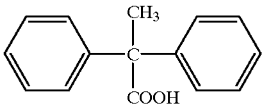
AII-4
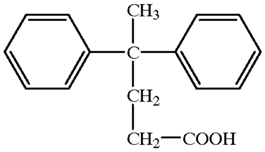
AII-5
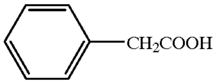
AII-6
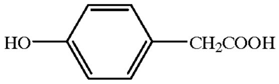
AII-7
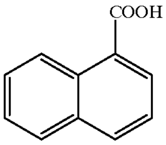
AII-8
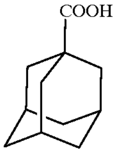
AII-9
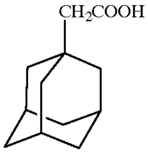
AII-10
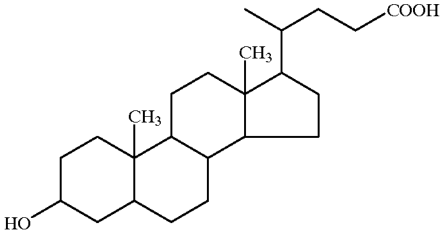

The compound bearing a ≡C—COOH group within the molecule may be used singly or as combinations of two or more thereof.

The compound bearing a ≡C—COOH group within the molecule is added in an amount ranging from 0 to 5 parts, preferably 0.1 to 5 parts, more preferably 0.1 to 3 parts, further preferably 0.1 to 2 parts, per 100 parts of the base resin. More than 5 parts of the compound can reduce the resolution of the resist composition.

The resist composition of the invention may additionally include an acetylene alcohol derivative for the purpose of enhancing the shelf stability. Preferred acetylene alcohol derivatives are those having the general formula (S1) or (S2) below.

S1

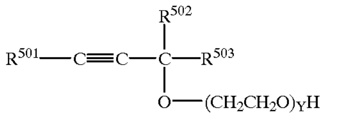

S2

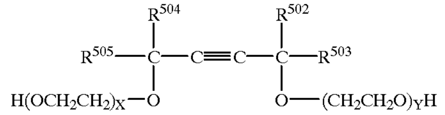

In the formulas, $R^{501}$, $R^{502}$, $R^{503}$, $R^{504}$, and $R^{505}$ are each hydrogen or a straight, branched, or cyclic alkyl of 1 to 8 carbon atoms; and X and Y are each 0 or a positive number, satisfying $0 \leqq X \leqq 30$, $0 \leqq Y \leqq 30$, and $0 \leqq X+Y \leqq 40$.

Preferable examples of the acetylene alcohol derivative include Surfynol 61, Surfynol 82, Surfynol 104, Surfynol 104E, Surfynol 104H, Surfynol 104A, Surfynol TG, Surfynol PC, Surfynol 440, Surfynol 465, and Surfynol 485 from Air Products and Chemicals Inc., and Surfynol E1004 from Nisshin Chemical Industry K.K.

The acetylene alcohol derivative is preferably added in an amount of 0.01 to 2% by weight, and more preferably 0.02 to 1% by weight, per 100% by weight of the resist composition. Less than 0.01% by weight would be ineffective for improving coating characteristics and shelf stability, whereas more than 2% by weight would result in a resist having a low resolution.

The resist composition of the invention may include, as an optional ingredient, a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Florade FC-430 and FC-431 from Sumitomo 3M K.K., Surflon S-141 and S-145 from Asahi Glass K.K., Unidine DS-401, DS-403 and DS-451 from Daikin Industry K.K., Megaface F-8151 from Dai-Nippon Ink & Chemicals K.K., and X-70-092 and X-70-093 from Shin-Etsu Chemical Co., Ltd. Preferred surfactants are Florade FC-430 from Sumitomo 3M K.K. and X-70-093 from Shin-Etsu Chemical Co., Ltd.

Pattern formation using the resist composition of the invention may be carried out by a known lithographic technique. For example, the resist composition is applied onto a substrate such as a silicon wafer by spin coating or the like to form a resist film having a thickness of 0.5 to 2.0 μm, which is then pre-baked on a hot plate at 60 to 150° C. for 1 to 10 minutes, and preferably at 80 to 120° C. for 1 to 5 minutes. A patterning mask having the desired pattern is then placed over the resist film, and the film exposed through the mask to an electron beam or to high-energy radiation such as deep-UV rays, an excimer laser, or x-rays in a dose of about 1 to 200 $mJ/cm^2$, and preferably about 10 to 100 $mJ/cm^2$, then post-exposure baked (PEB) on a hot plate at 60 to 150° C. for 1 to 5 minutes, and preferably at 80 to 120° C. for 1 to 3 minutes. Finally, development is carried out using as the developer an aqueous alkali solution, such as a 0.1 to 5% (preferably 2 to 3%) aqueous solution of tetramethylammonium hydroxide (TMAH), this being done by a conventional method such as dipping, puddling, or spraying for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV rays having a wavelength of 193 to 248 nm, an excimer laser, x-rays, or an electron beam. The desired pattern may not be obtainable outside the upper and lower limits of the above range.

The resist composition comprising the polymer of the invention as a base resin lends itself to micropatterning with electron beams or deep-UV rays since it is sensitive to high-energy radiation and has excellent sensitivity, resolution, and etching resistance. Especially because of the minimized absorption at the exposure wavelength of an ArF or KrF excimer laser, a finely defined pattern having side-walls perpendicular to the substrate can easily be formed.

EXAMPLE

Examples of the invention are given below by way of illustration and not by way of limitation.

First described are examples of synthesizing 2-alkylbicyclo[2.2.1]heptan-2-yl ester compounds in exo-form according to the invention and examples of preparing polymers therefrom.

Synthetic Example 1-1

Synthesis of Monomer 1

In 600 ml of tetrahydrofuran was dissolved 148.5 g of ethyl bromide. Below 60° C., this reaction mixture was added dropwise to 32.4 g of metallic magnesium over one hour. After agitation was continued for 2 hours at room temperature, 150.0 g of tricyclo[5.2.1.$0^{2,6}$]decan-8-one was added dropwise over 45 minutes to the reaction mixture which was kept below 65° C. After agitation was continued for one hour at room temperature, the reaction solution was worked up in a conventional manner. The resulting oily substance was distilled in vacuum, collecting 157.7 g of 8-ethyltricyclo[5.2.1.$0^{2,6}$]decan-8-ol in endo-form. The yield was 87.6%.

In 600 ml of benzene was dissolved 155.0 g of 8-ethyltricyclo[5.2.1.$0^{2,6}$ ]decan-8-ol in endo-form. To the solution was added 8.2 g of p-toluenesulfonic acid monohydrate. This reaction mixture was heated, agitated under reflux for 6 hours while removing water, and subjected to conventional post-treatment. The resulting oily substance was purified by silica gel column chromatography, obtaining 105.0 g of 8-ethylidenetricyclo[5.2.1.$0^{2,6}$]decane. The yield was 75.3%.

In 500 ml of methylene chloride wets dissolved 103.0 g of 8-ethylidenetricyclo[5.2.1.$0^{2,6}$]decane. To this solution was added 202.5 g of 65% m-chloroperbenzoic acid. This reaction mixture was agitated for 12 hours at 4° C. and subjected to conventional post-treatment, obtaining an oily substance. This was used in the subsequent reaction without purification.

The oily substance obtained in the above step was dissolved in 200 ml of diethyl ether. With stirring, this solution was added dropwise to a suspension of 24.2 g of aluminum lithium hydride in 200 ml of tiethyl ether under ice cooling. The reaction mixture was agitated for a further 2 hours at room temperature and subjected to conventional post-treatment. The resulting oily substance was distilled in vacuum, obtaining 102.4 g of 8-ethyltricyclo[5.2.1.$0^{2,6}$]decan-8-ol in exo-form. The yield was 89.5%.

In 400 ml of methylene chloride was dissolved 101.0 g of 8-ethyltricyclo[5.2.1.$0^{2,6}$]decan-8-ol in exo-form. With stirring, 88.0 g of methacrylic acid chloride and then 170.0 g of triethylamine were added dropwise to the solution under ice cooling. The reaction mixture was agitated for a further 12 hours at room temperature and subjected to conventional post-treatment. The resulting oily substance was distilled in vacuum, collecting 105.5 g of 8-ethyltricyclo[5.2.1.$0^{2,6}$]decan-8-yl methacrylate in exo-form, designated Monomer 1. The yield was 75.8%.

$^1$H-NMR ($CDCl_3$, 270 MHz): δ0.81 (t, 3H), 0.85–1.05 (2H, m), 1.21 (m, 1H), 1.30 (dd, 1H), 1.37 (m, 1H), 1.44 (m, 1H), 1.60–2.10 (m, 11H), 2.22 (m, 1H), 2.39 (m, 1H), 5.46 (m, 1H), 6.01 (m, 1H)

FT-IR: 2951, 2864, 1713, 1637, 1448, 1331, 1304, 1182, 1157 $cm^{-1}$

Synthetic Example 1-2

Synthesis of Monomer 2

By following the same procedure as above, 8-isopropyltricyclo[5.2.1.$0^{2,6}$]decan-8-yl methacrylate in exo-form, designated Monomer 2, was synthesized from tricyclo[5.2.1.$0^{2,6}$ ]decan-8-one.

$^1$H-NMR ($CDCl_3$, 270 MHz):0.97 (d, 3H), 1.06 (d, 3H), 0.85–1.45 (6H, m), 1.60–2.10 (10H, m), 2.22 (dd, 1H), 3.02 (m, 1H), 5.45 (m, 1H), 5.99 (m, 1H)

FT-IR: 2956, 2864, 1713, 1637, 1450, 1319, 1300, 1182, 1157 $cm^{-1}$

Synthetic Example 1-3

Synthesis of Monomer 3

By following the same procedure as above, 8-methyltricyclo[5.2.1.$0^{2,6}$ ]decan-8-yl methacrylate in exo-form, designated Monomer 3, was synthesized from tricyclo[5.2.1.$0^{2,6}$]decan-8-one.

$^1$H-NMR ($CDCl_3$, 270 MHz): δ0.85–1.05 (m, 2H), 1.21 (m, 1H), 1.30 (dd, 1H), 1.35 (m, 1H), 1.46 (m, 1H), 1.56 (s, 3H), 1.60–2.15 (m, 10H), 2.39 (m, 1H), 5.46 (m, 1H), 5.99 (m, 1H)

FT-IR: 2949, 2864, 1711, 1637, 1450, 1331, 1303, 1174, 1151, 1054 $cm^{-1}$

Synthetic Example 1-4

Synthesis of Monomer 4

By following the same procedure as above, 2-ethylbicyclo[2.2.1]heptan-2-yl methacrylate in exo-form, designated Monomer 4, was synthesized from bicyclo[2.2.1]heptan-2-one.

$^1$H-NMR ($CDCl_3$, 270 MHz): δ80.80 (t, 3H), 1.08 (m, 1H), 1.21 (m, 1H), 1.30–1.60 (2H, m), 1.68 (m, 1H), 1.83 (m, 1H), 1.89 (m, 3H), 2.02 (m, 1H), 2.20–2.35 (m, 2H), 2.59 (m, 1H), 5.46 (m, 1H), 6.01 (m, 1H)

FT-IR: 2966, 2879, 1713, 1637, 1456, 1327, 1311, 1309, 1167 $cm^{-1}$

Synthetic Example 1-5

Synthesis of Monomer 5

By following the same procedure as above, 2-isopropylbicyclo[2.2.1]heptan-2-yl methacrylate in exo-form, designated Monomer 5, was synthesized from bicyclo[2.2.1]heptan-2-one.

$^1$H-NMR ($CDCl_3$, 270 MHz): δ0.98 (d, 3H), 1.03 (d, 3H), 0.80–1.70 (8H, m), 1.80–2.00 (m, 4H), 2.22 (m, 1H), 3.19 (m, 1H), 5.45 (m, 1H), 5.98 (m, 1H)

FT-IR: 2964, 2873, 1713, 1637, 1454, 1325, 1300, 1174, 1155 $cm^{-1}$

Synthetic Example 1-6

Synthesis of Monomer 6

By following the same procedure as above, 2-ethylbicyclo[2.2.1]heptan-2-yl acrylate in exo-form, designated Monomer 6, was synthesized from bicyclo[2.2.1]heptan-2-one.

$^1$H-NMR ($CDCl_3$, 270 MHz): δ0.80 (t, 3H), 1.06 (m, 1H), 1.20 (m, 1H), 1.30–1.60 (m, 4H), 1.68 (m, 1H), 1.82 (dq, 1H), 2.01 (m, 1H), 2.22 (m, 1H), 2.51 (dq, 1H), 2.58 (m, 1H), 5.71 (dd, 1H), 6.04 (dd, 1H), 6.29 (m, 1H)

FT-IR: 2968, 2879, 1718, 1635, 1620, 1458, 1402, 1288, 1272, 1227, 1200, 1173, 1133, 1115, 1107, 1047 $cm^{-1}$

Synthetic Examples 7 to 18

Synthesis of Monomers 7 to 18

Monomers 7 to 18 were synthesized by the same procedure as above.

Monomer 1

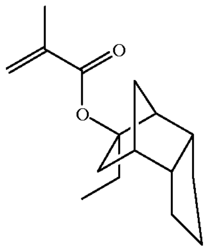

Monomer 2

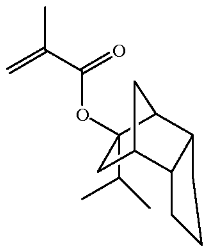

-continued
Monomer 3
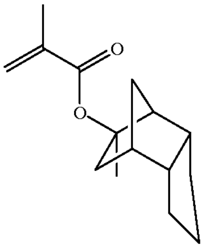
Monomer 4
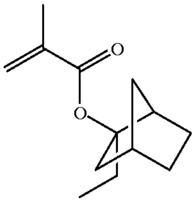
Monomer 5
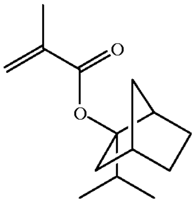
Monomer 6
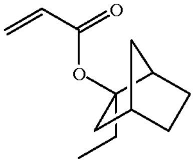
Monomer 7
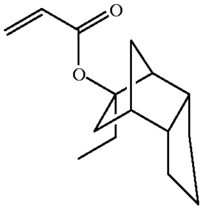
Monomer 8
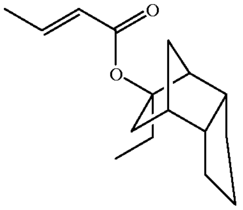
Monomer 9
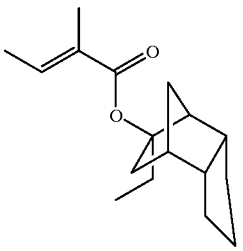
-continued
Monomer 10
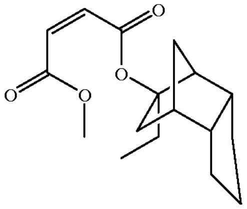
Monomer 11
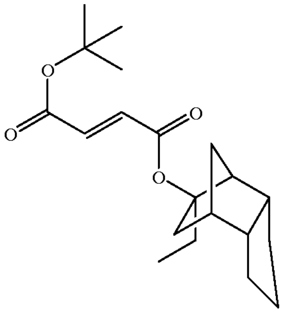
Monomer 12
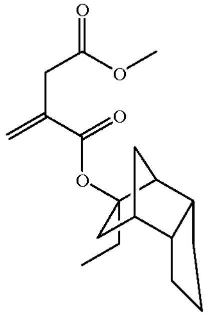
Monomer 13
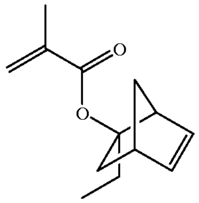
Monomer 14
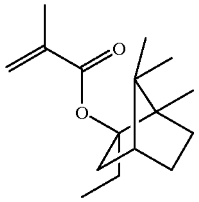
Monomer 15
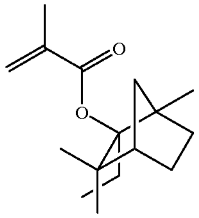

-continued

Monomer 16

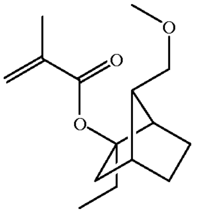

Monomer 17

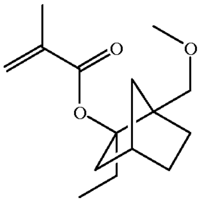

Monomer 18

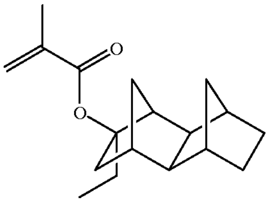

Synthetic Example 2-1

Synthesis of Polymer 1

In 200 ml of tetrahydrofuran, 17.4 g of Monomer 1 and 5.5 g of 5-methyl-2-oxooxolan-5-yl methacrylate were dissolved, and 1.3 g of 2,2'-azobisisobutyronitrile added. After agitation was continued for 15 hours at 60° C., the reaction solution was concentrated in vacuum. The residue was dissolved in 80 ml of tetrahydrofuran and added dropwise to 2 liters of n-hexane. The resulting solids were collected by filtration, washed with 2 liters of n-hexane, and dried in vacuum at 40° C. for 6 hours, obtaining 14.4 g of a polymer, designated Polymer 1. The yield was 62.7%.

Synthetic Examples 2-2 to 2-56

Synthesis of Polymers 2 to 56

Polymers 2 to 56 were synthesized as in Synthetic Example 2–1.

(Polymer 1)

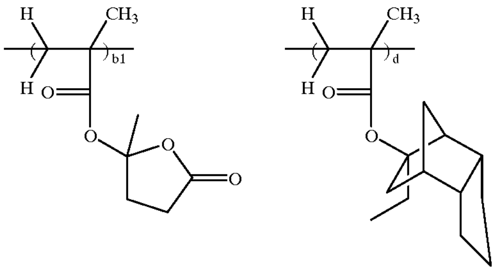

(b1 = 0.30, d = 0.70, Mw = 11,500)

-continued (Polymer 2)

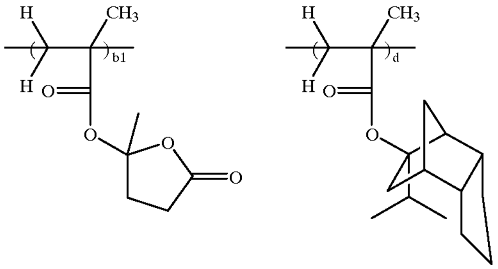

(b1 = 0.30, d = 0.70, Mw = 11,900)

(Polymer 3)

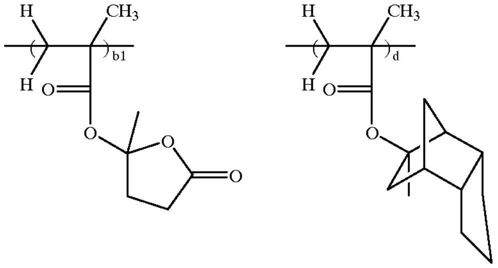

(b1 = 0.30, d = 0.70, Mw = 11,000)

(Polymer 4)

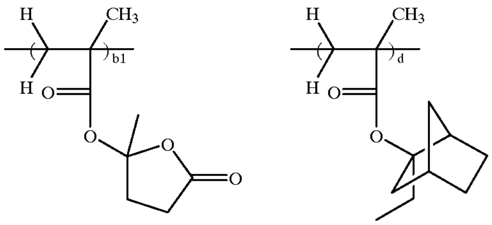

(b1 = 0.30, d = 0.70, Mw = 10,100)

(Polymer 5)

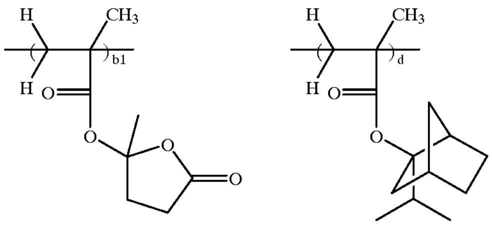

(b1 = 0.30, d = 0.70, Mw = 10,500)

(Polymer 6)

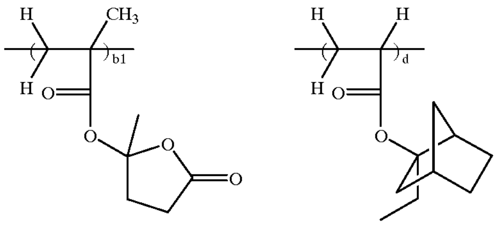

(b1 = 0.30, d = 0.70, Mw = 9,600)

-continued
(Polymer 7)
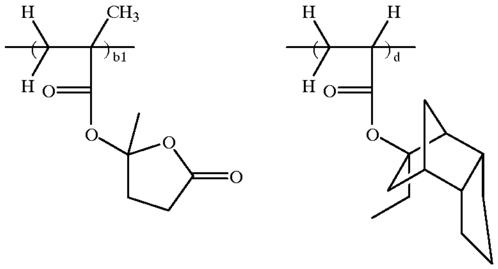
(b1 = 0.30, d = 0.70, Mw = 11,000)
(Polymer 8)
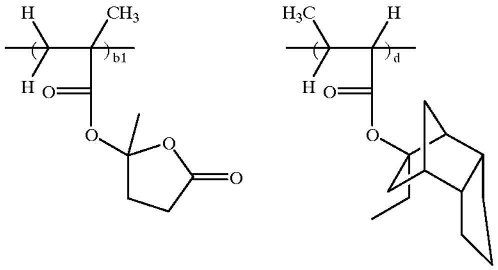
(b1 = 0.30, d = 0.70, Mw = 11,500)
(Polymer 9)
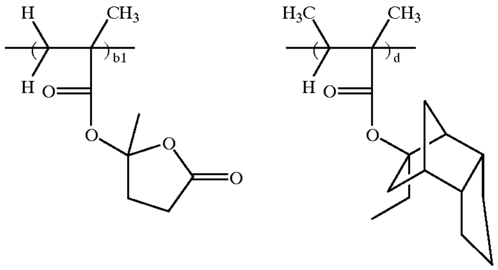
(b1 = 0.30, d = 0.70, Mw = 11,900)
(Polymer 10)
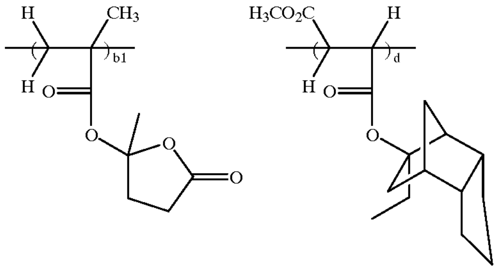
(b1 = 0.30, d = 0.70, Mw = 13,000)
(Polymer 11)
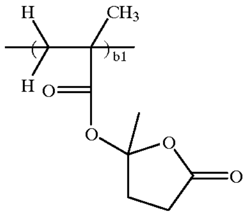
-continued
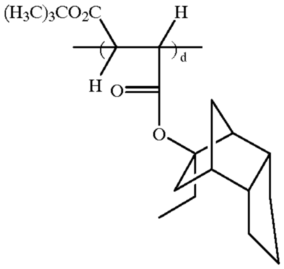
(b1 = 0.30, d = 0.70, Mw = 14,500)
(Polymer 12)
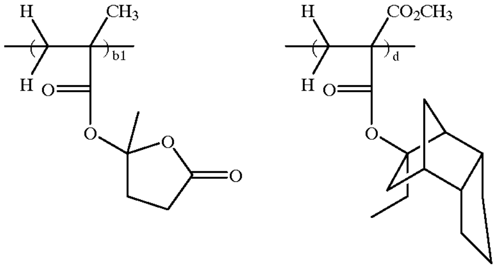
(b1 = 0.30, d = 0.70, Mw = 13,500)
(Polymer 13)
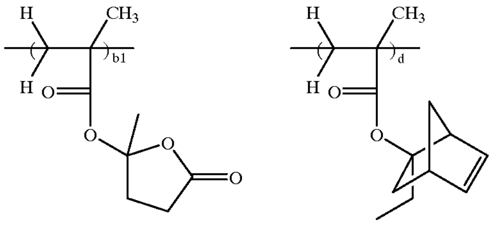
(b1 = 0.30, d = 0.70, Mw = 10,000)
(Polymer 14)
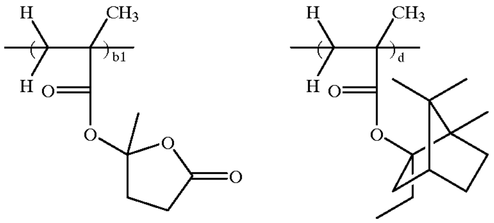
(b1 = 0.30, d = 0.70, Mw = 11,500)
(Polymer 15)
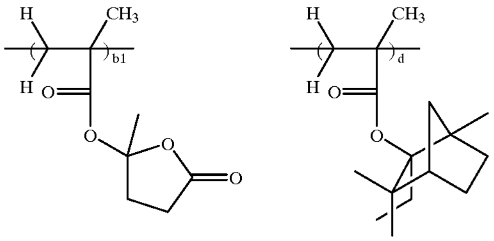
(b1 = 0.30, d = 0.70, Mw = 11,500)

-continued
(Polymer 16)
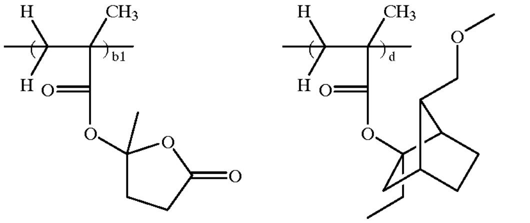
(b1 = 0.30, d = 0.70, Mw = 11,600)
(Polymer 17)
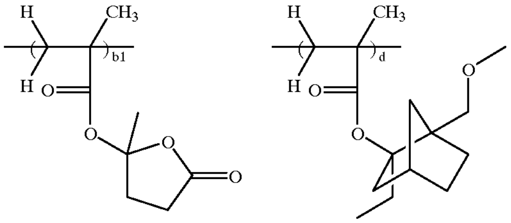
(b1 = 0.30, d = 0.70, Mw = 11,600)
(Polymer 18)
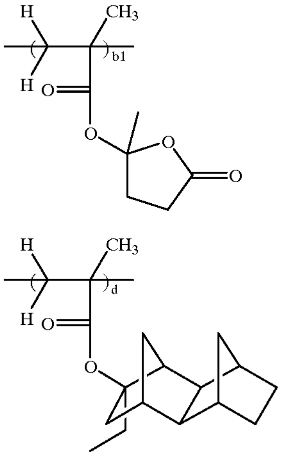
(b1 = 0.30, d = 0.70, Mw = 12,400)
(Polymer 19)
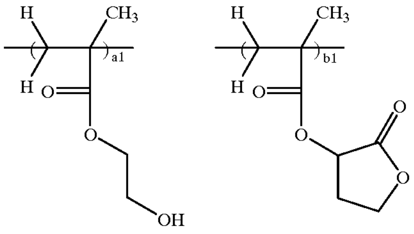
-continued
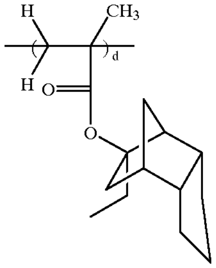
(a1 = 0.20, b1 = 0.20, d = 0.60, Mw = 10,500)
(Polymer 20)
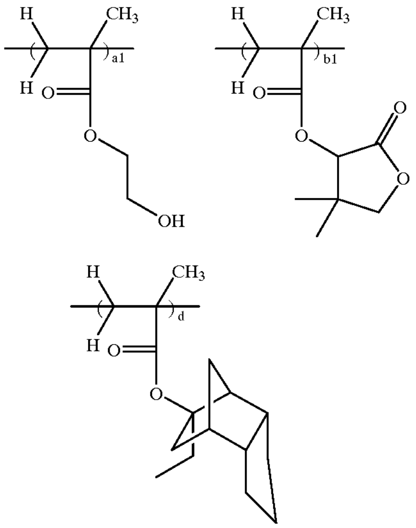
(a1 = 0.20, b1 = 0.20, d = 0.60, Mw = 10,700)
(Polymer 21)
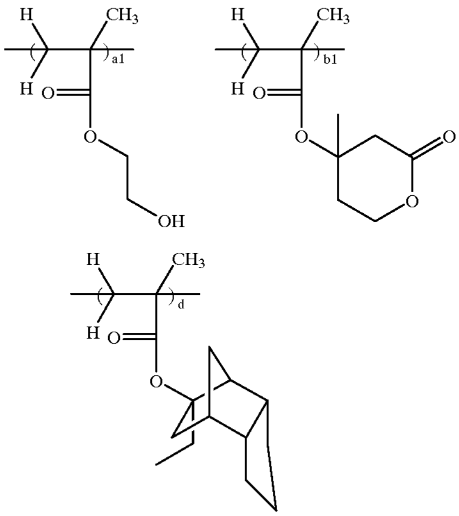
(a1 = 0.20, b1 = 0.20, d = 0.60, Mw = 10,700)

-continued
(Polymer 22)
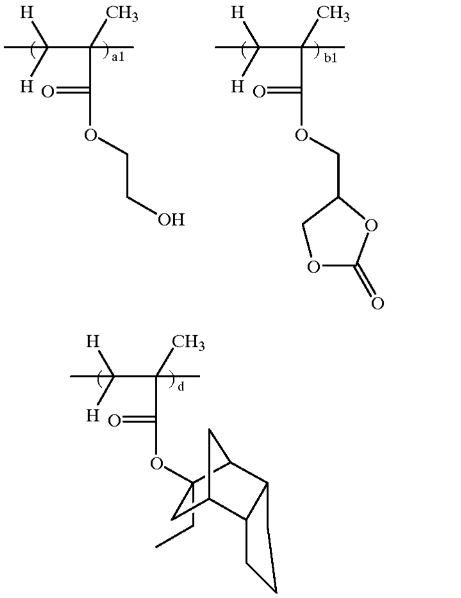
(a1 = 0.20, b1 = 0.20, d = 0.60, Mw = 10,600)
(Polymer 23)
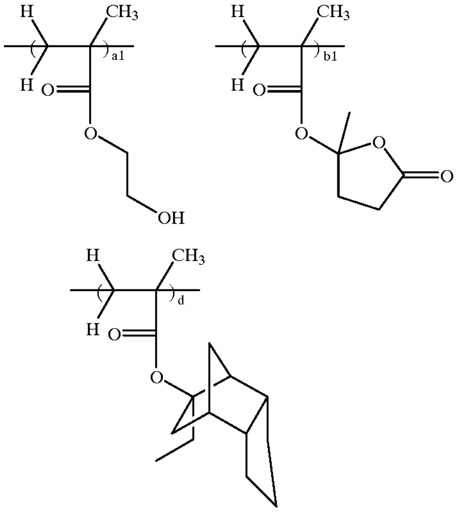
(a1 = 0.20, b1 = 0.20, d = 0.60, Mw = 10,600)
(Polymer 24)
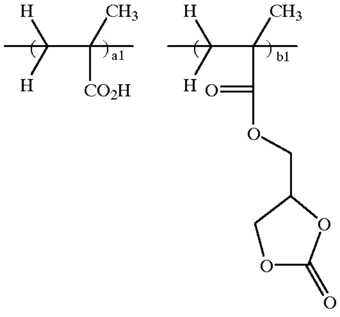
-continued
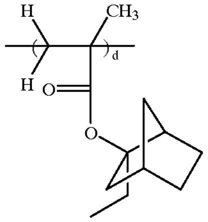
(a1 = 0.20, b1 = 0.20, d = 0.60, Mw = 9,000)
(Polymer 25)
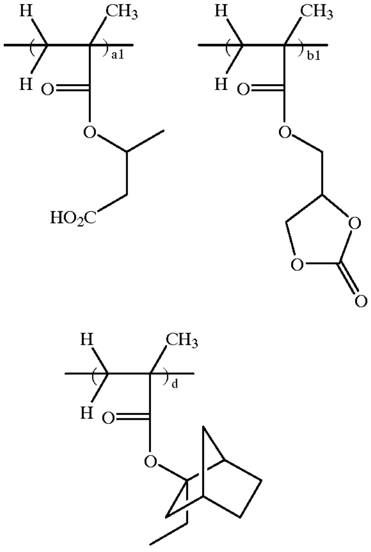
(a1 = 0.20, b1 = 0.20, d = 0.60, Mw = 9,800)
(Polymer 26)
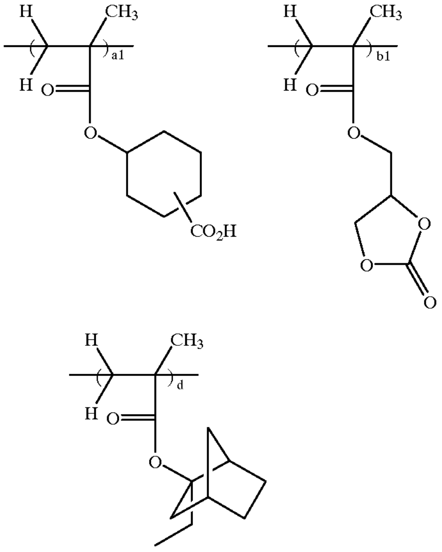
(a1 = 0.20, b1 = 0.20, d = 0.60, Mw =10,200)

-continued
(Polymer 27)
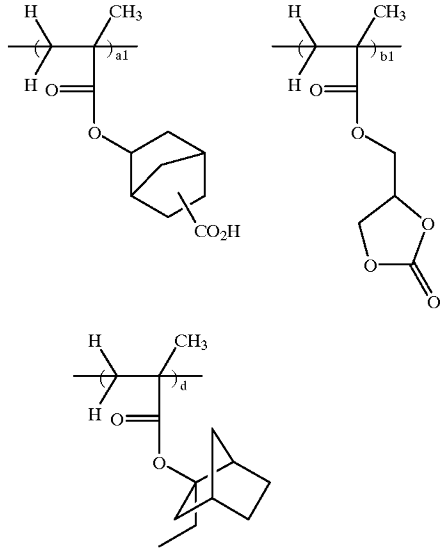
(a1 = 0.20, b1 = 0.20, d = 0.60, Mw =10,400)
(Polymer 28)
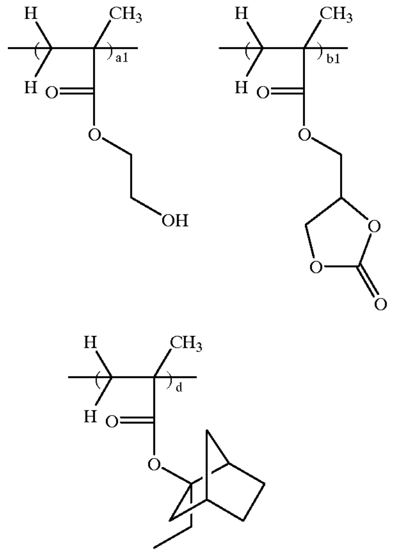
(a1 = 0.20, b1 = 0.20, d = 0.60, Mw = 9,400)
(Polymer 29)
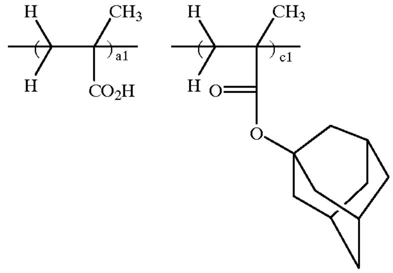
-continued
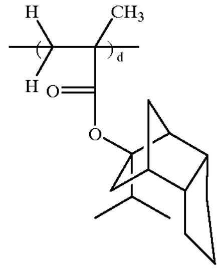
(a1 = 0.20, c1 = 0.30, d = 0.50, Mw = 10,700)
(Polymer 30)
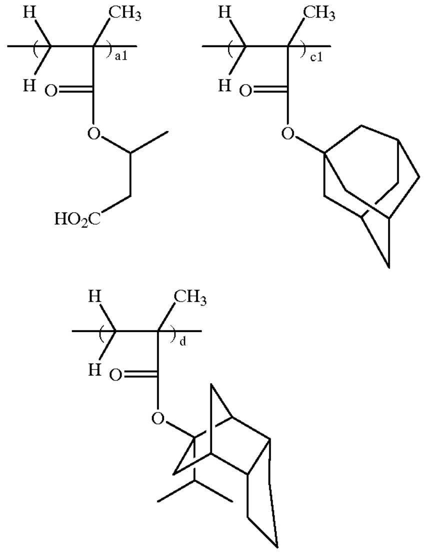
(a1 = 0.20, c1 = 0.30, d = 0.50, Mw = 11,600)
(Polymer 31)
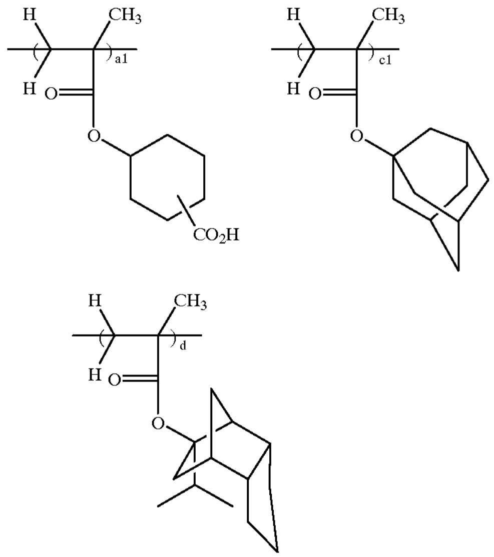
(a1 = 0.20, c1 = 0.30, d = 0.50, Mw = 12,000)

-continued
(Polymer 32)
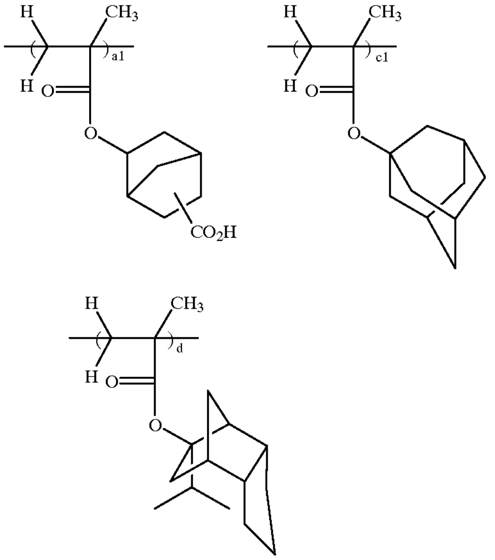
(a1 = 0.20, c1 = 0.30, d = 0.50, Mw = 12,100)
(Polymer 33)
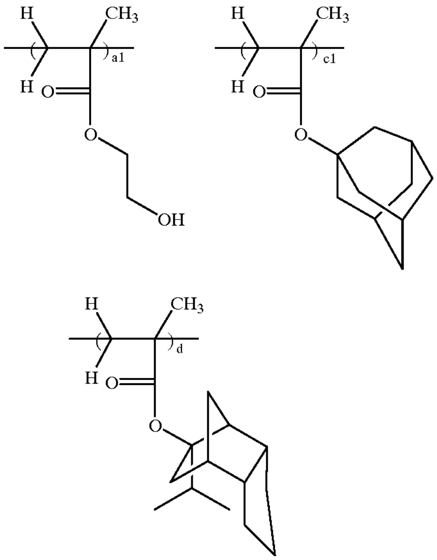
(a1 = 0.20, c1 = 0.30, d = 0.50, Mw = 11,200)
(Polymer 34)
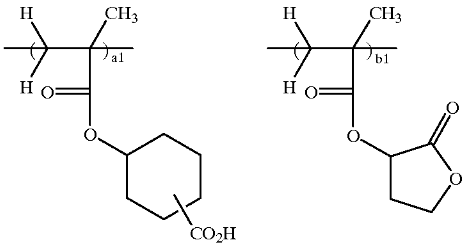
-continued
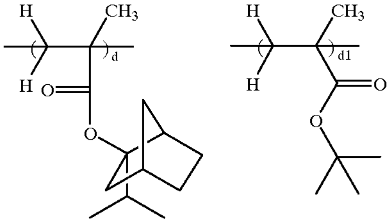
(a1 = 0.20, b1 = 0.20, d = 0.40, d1 = 0.20, Mw = 19,400)
(Polymer 35)
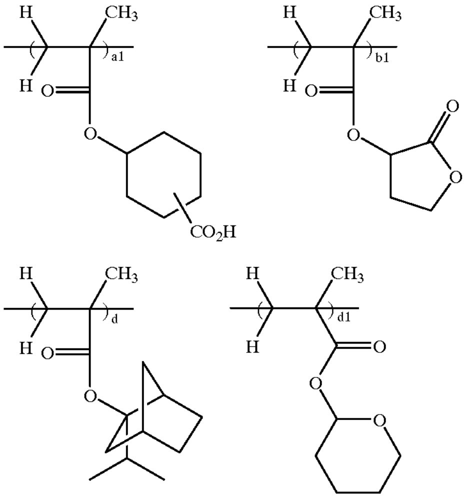
(a1 = 0.20, b1 = 0.20, d = 0.40, d1 = 0.20, Mw = 19,900)
(Polymer 36)
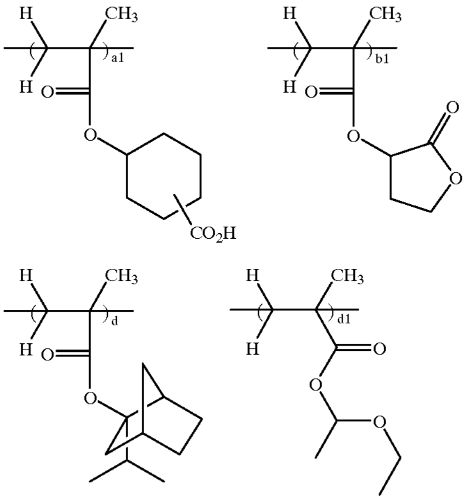
(a1 = 0.20, b1 = 0.20, d = 0.40, d1 = 0.20, Mw = 19,700)

-continued
(Polymer 37)
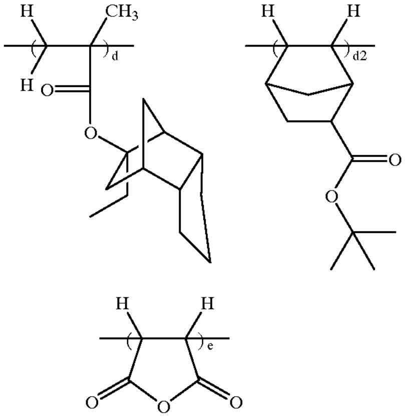
(d = 0.40, d2 = 0.30, e = 0.30, Mw = 4,700)
(Polymer 38)
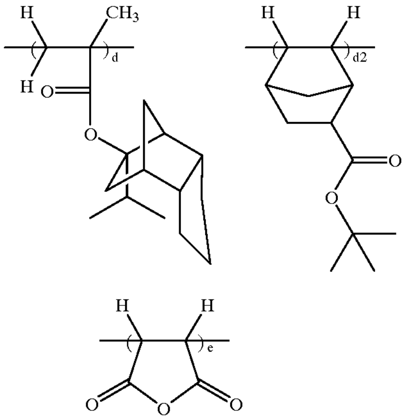
(d = 0.40, d2 = 0.30, e = 0.30, Mw = 4,800)
(Polymer 39)
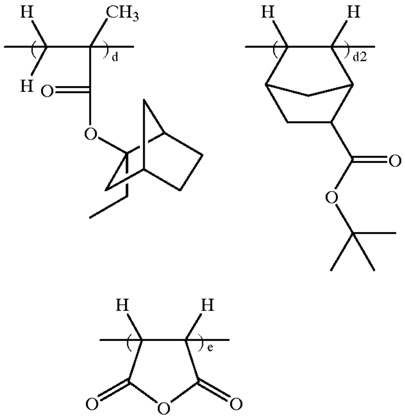
(d = 0.40, d2 = 0.30, e = 0.30, Mw = 4,300)
-continued
(Polymer 40)
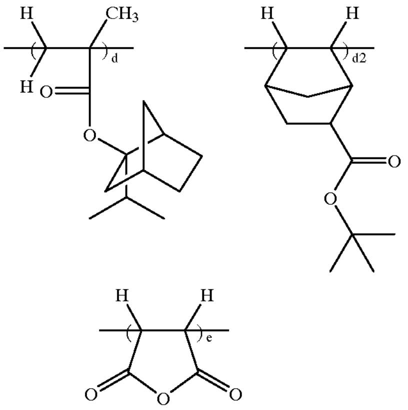
(d = 0.40, d2 = 0.30, e = 0.30, Mw = 4,400)
(Polymer 41)
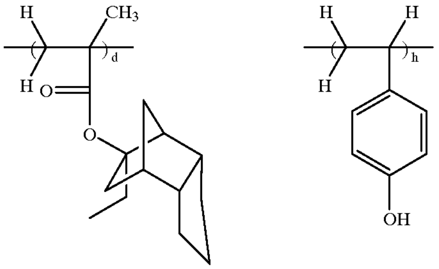
(d = 0.35, h = 0.65, Mw = 13,200)
(Polymer 42)
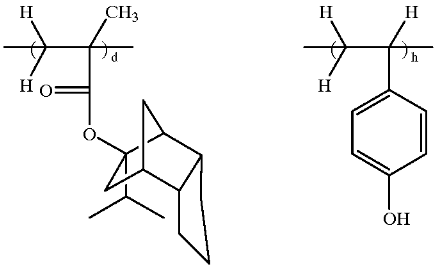
(d = 0.35, h = 0.65, Mw = 13,600)
(Polymer 43)
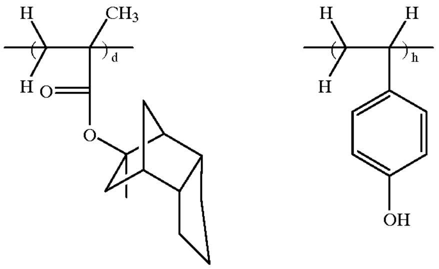
(d = 0.35, h = 0.65, Mw = 12,800)

-continued
(Polymer 44)
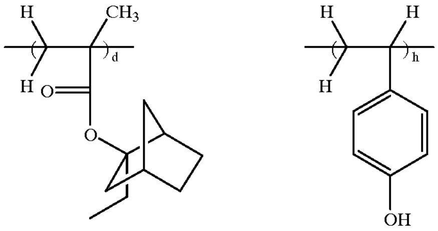
(d = 0.35, h = 0.65, Mw = 12,100)
(Polymer 45)
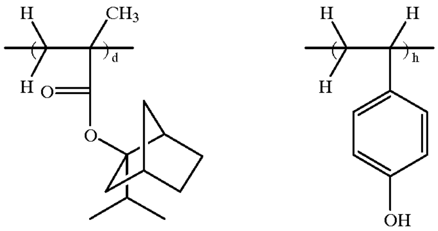
(d = 0.35, h = 0.65, Mw = 12,500)
(Polymer 46)
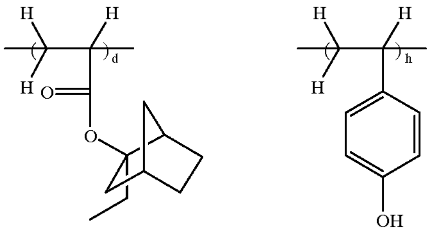
(d = 0.35, h = 0.65, Mw = 11,700)
(Polymer 47)
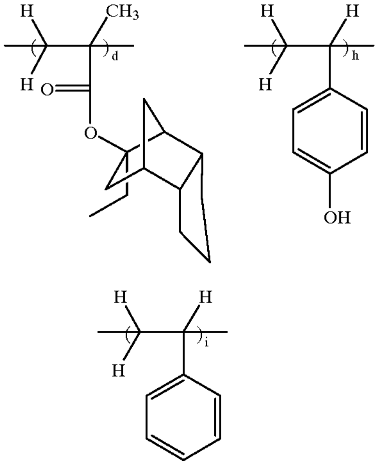
(d = 0.40, h = 0.40, i = 0.20, Mw = 13,500)
-continued
(Polymer 48)
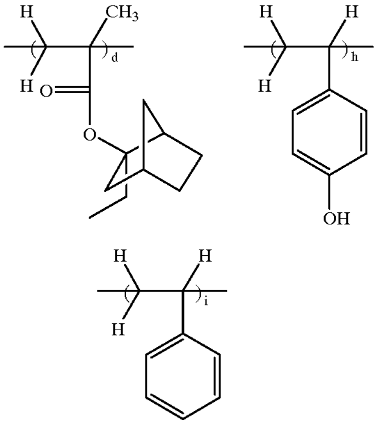
(d = 0.40, h = 0.40, i = 0.20, Mw = 12,200)
(Polymer 49)
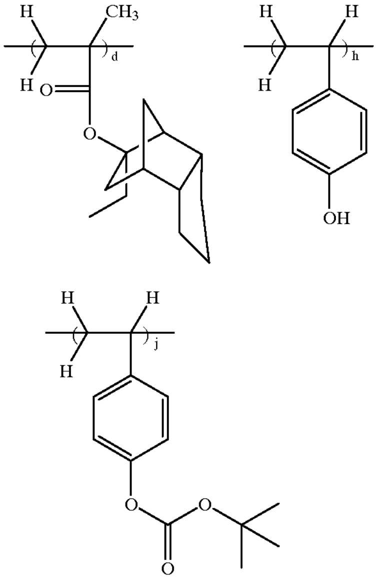
(d = 0.25, h = 0.65, j = 0.10, Mw = 13,000)
(Polymer 50)
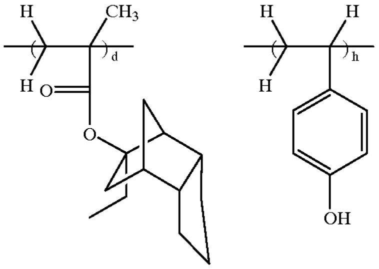

-continued
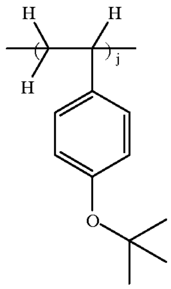
(d = 0.25, h = 0.65, j = 0.10, Mw = 12,600)
(Polymer 51)
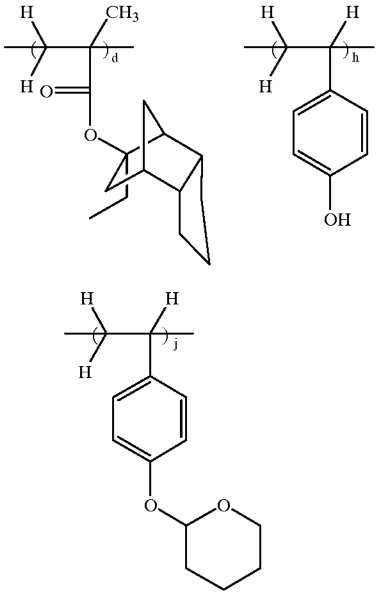
(d = 0.25, h = 0.65, j = 0.10, Mw = 12,800)
(Polymer 52)
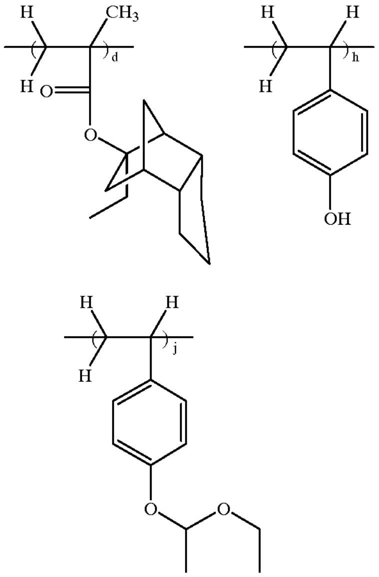
(d = 0.25, h = 0.65, j = 0.10, Mw = 12,800)
-continued
(Polymer 53)
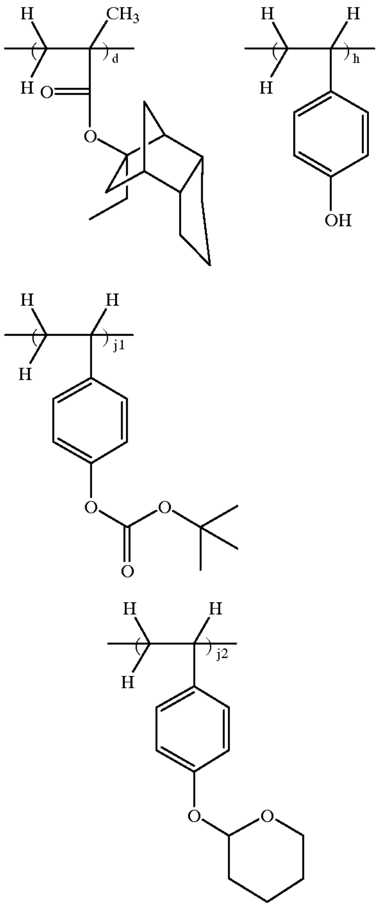
(d = 0.20, h = 0.65, j1 = 0.05, j2 = 0.10, Mw = 12,700)
(Polymer 54)
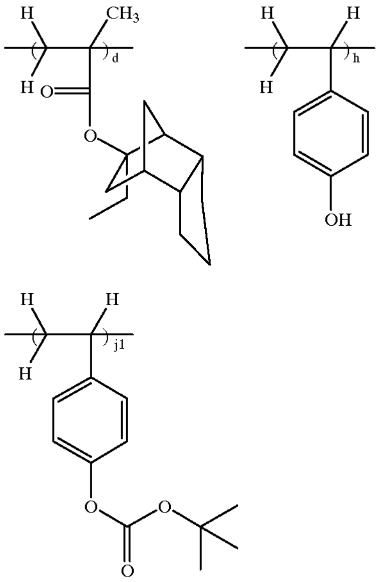

-continued

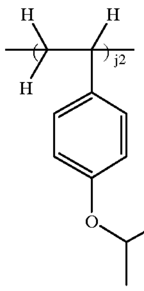

(d = 0.20, h = 0.65, j1 = 0.05, j2 = 0.10, Mw = 12,600)

(Polymer 55)

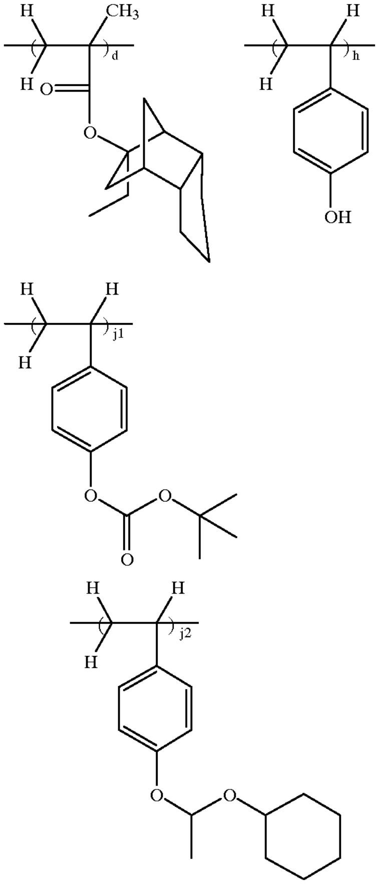

(d = 0.20, h = 0.65, j1 = 0.05, j2 = 0.10, Mw = 13,100)

(Polymer 56)

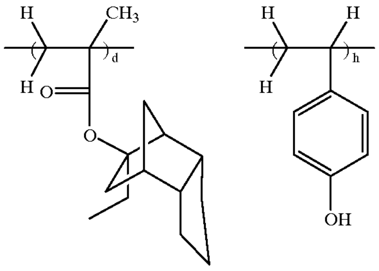

-continued

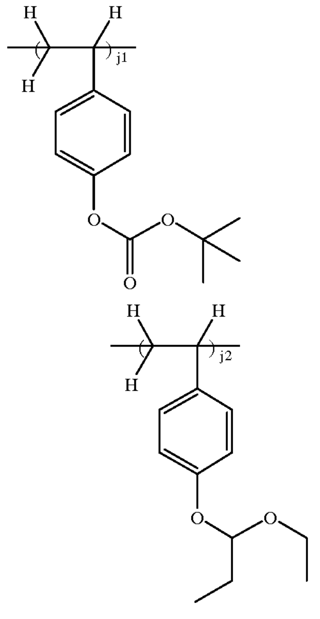

(d = 0.20, h = 0.65, j1 = 0.05, j2 = 0.10, Mw = 12,800)

Example I

Resist compositions were formulated using Polymers 1 to 40 obtained in the above Synthetic Examples and examined for resolution.

Examples I1 to I-80: Evaluation of resist resolution

Resist compositions were prepared by using Polymers 1 to 40 or Polymers 57 to 64 shown below as the base resin, and dissolving the polymer, a photoacid generator (designated as PAG 1 to 8), a dissolution inhibitor (designated as $DRR^1$ to 4), a basic compound, and a compound having a ≡C—COOH group in the molecule (ACC 1) in a solvent containing 0.05% by weight of surfactant Florade FC-430 (Sumitomo 3M) in the combination shown in the following Tables. These compositions were each filtered through a 0.2-μm Teflon filter, thereby giving resist solutions.

(Polymer 57)

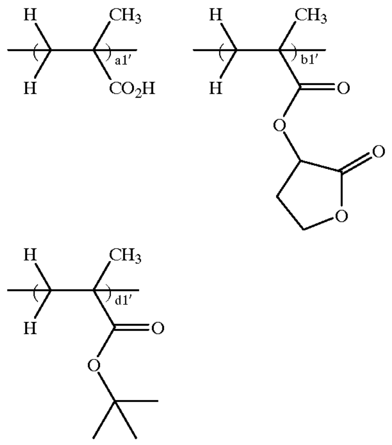

(a1' = 0.10, b1' = 0.20, d1' = 0.70, Mw = 7,100)

-continued
(Polymer 58)
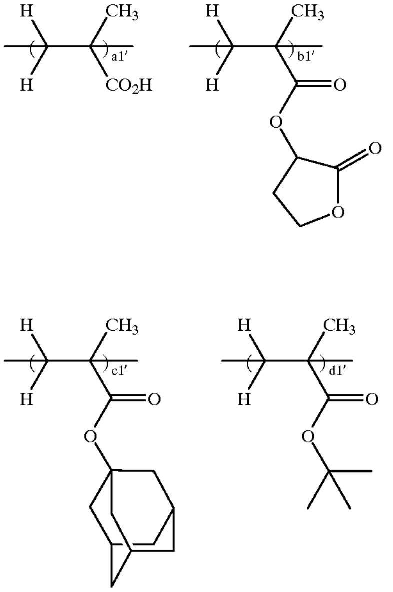
(a1′ = 0.10, b1′ = 0.20, c1′ = 0.20, d1′ = 0.50, Mw = 7,900)
(Polymer 59)
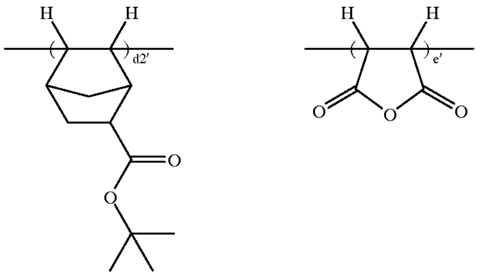
(d2′ = 0.50, e′ = 0.50, Mw = 7,300)
(Polymer 60)
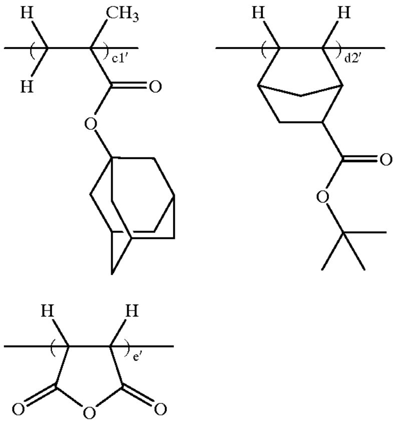
(c1′ = 0.20, d2′ = 0.40, e′ = 0.40, Mw = 8,000)
-continued
(Polymer 61)
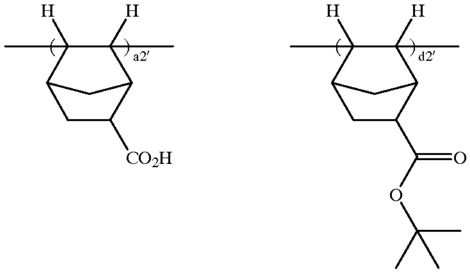
(a2′ = 0.20, d2′ = 0.80, Mw = 27,500)
(Polymer 62)
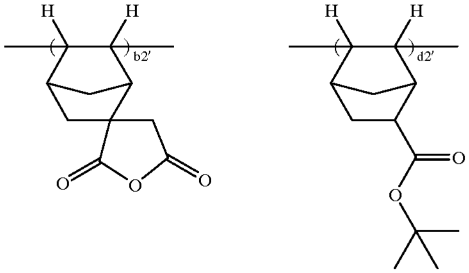
(b2′ = 0.30, d2′ = 0.70, Mw = 28,400)
(Polymer 63)
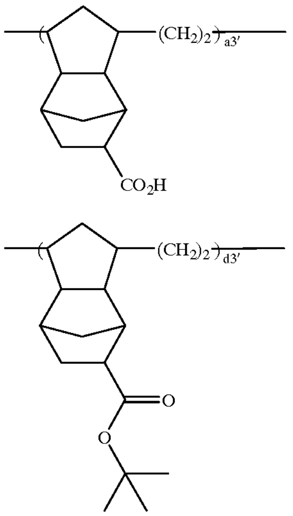
(a3′ = 0.20, d3′ = 0.80, Mw = 50,200)
(Polymer 64)
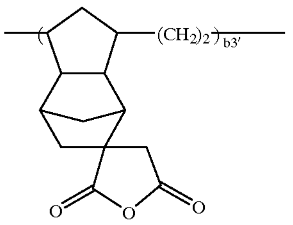

-continued

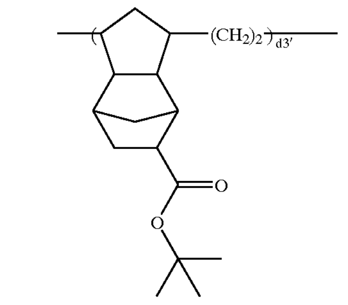

(b3' = 0.30, d3' = 0.70, Mw = 51,500)

(PAG 1)

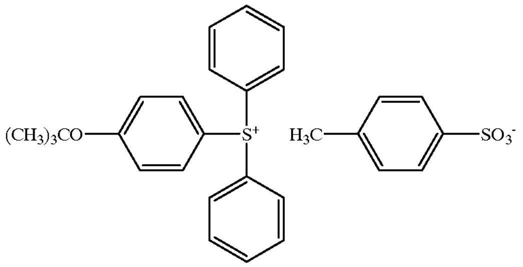

(PAG 2)

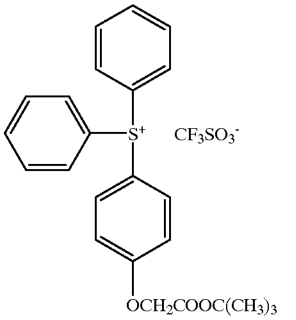

(PAG 3)

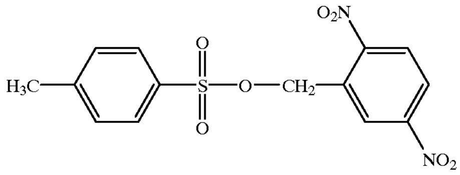

(PAG 4)

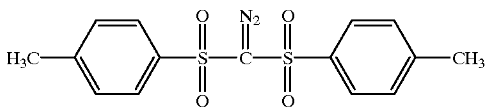

(PAG 5)

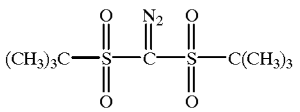

(PAG 6)

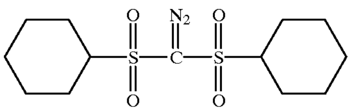

-continued (PAG 7)

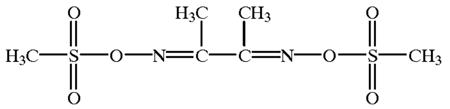

(PAG 8)

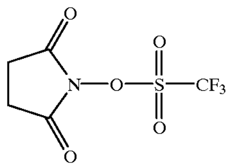

(DRR 1)

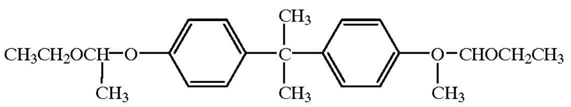

(DRR 2)

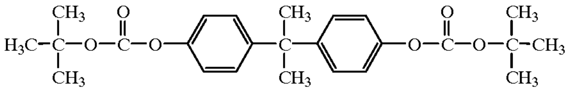

(DRR 3)

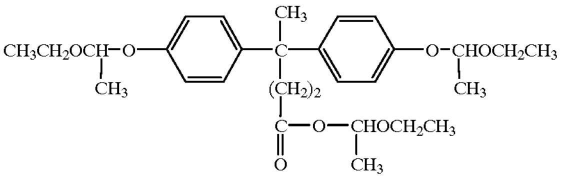

(DRR 4)

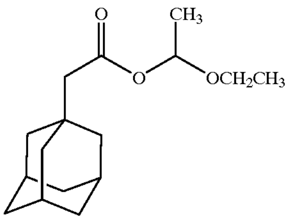

(ACC1)

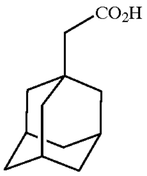

The solvents and basic compounds used are as follows.

PGMEA: propylene glycol methyl ether acetate

PG/EL: a mixture of 70% PGMEA and 30% ethyl lactate

TBA: tributylamine

TEA: triethanolamine

TMMEA: trismethoxymethoxyethylamine

TMEMEA: trismethoxyethoxymethoxyethylanine

These resist solutions were spin-coated onto silicon wafers, then baked at 110° C. for 90 seconds on a hot plate to give resist films having a thickness of 0.5 μm. The resist films were exposed using an ArF excimer laser stepper (Nikon Corporation; NA 0.55), then baked (PEB) at 110° C. for 90 seconds, and developed with a solution of 2.38% tetramethylammonium hydroxide in water, thereby giving positive patterns.

The resulting resist patterns were evaluated as described below.

First, the sensitivity (Eth, mJ/$cm^2$) was determined. Next, the optimal dose (sensitivity Eop, mJ/$cm^2$) was defined as the dose which provides a 1:1 resolution at the top and bottom of a 0.25 μm line-and-space pattern, and the resolution of the resist under evaluation was defined as the minimum line width (μm) of the lines and spaces that separated at this dose. The shape of the resolved resist pattern was examined under a scanning electron microscope.

The composition and test results of the resist materials are shown in Tables 1 to 5.

TABLE 1

| Example | Base resin | Photoacid generator | Dissolution inhibitor | Basic compound | Solvent | Sensitivity | Resolution | Shape |
|---|---|---|---|---|---|---|---|---|
| I-1 | Polymer 1 (80) | PAG 1 (2) | | TBA (0.125) | PGMEA (600) | 5.5 | 0.18 | rectangular |
| I-2 | Polymer 2 (80) | PAG 1 (2) | | TBA (0.125) | PGMEA (600) | 5.0 | 0.18 | rectangular |
| I-3 | Polymer 3 (80) | PAG 1 (2) | | TBA (0.125) | PGMEA (600) | 5.8 | 0.18 | rectangular |
| I-4 | Polymer 4 (80) | PAG 1 (2) | | TBA (0.125) | PGMEA (600) | 5.7 | 0.18 | rectangular |
| I-5 | Polymer 5 (80) | PAG 1 (2) | | TBA (0.125) | PGMEA (600) | 5.2 | 0.18 | rectangular |
| I-6 | Polymer 6 (80) | PAG 1 (2) | | TBA (0.125) | PGMEA (600) | 6.0 | 0.18 | rectangular |
| I-7 | Polymer 7 (80) | PAG 1 (2) | | TBA (0.125) | PGMEA (600) | 5.5 | 0.18 | rectangular |
| I-8 | Polymer 8 (80) | PAG 1 (2) | | TBA (0.125) | PGMEA (600) | 5.5 | 0.20 | rectangular |
| I-9 | Polymer 9 (80) | PAG 1 (2) | | TBA (0.125) | PGMEA (600) | 5.5 | 0.18 | rectangular |
| I-10 | Polymer 10 (80) | PAG 1 (2) | | TBA (0.125) | PGMEA (600) | 5.4 | 0.20 | rectangular |
| I-11 | Polymer 11 (80) | PAG 1 (2) | | TBA (0.125) | PGMEA (600) | 5.2 | 0.20 | rectangular |
| I-12 | Polymer 12 (80) | PAG 1 (2) | | TBA (0.125) | PGMEA (600) | 5.4 | 0.20 | rectangular |
| I-13 | Polymer 13 (80) | PAG 1 (2) | | TBA (0.125) | PGMEA (600) | 5.8 | 0.18 | rectangular |
| I-14 | Polymer 14 (80) | PAG 1 (2) | | TBA (0.125) | PGMEA (600) | 5.6 | 0.18 | rectangular |
| I-15 | Polymer 15 (80) | PAG 1 (2) | | TBA (0.125) | PGMEA (600) | 5.6 | 0.18 | rectangular |
| I-16 | Polymer 16 (80) | PAG 1 (2) | | TBA (0.125) | PGMEA (600) | 5.5 | 0.18 | rectangular |
| I-17 | Polymer 17 (80) | PAG 1 (2) | | TBA (0.125) | PGMEA (600) | 5.5 | 0.18 | rectangular |
| I-18 | Polymer 18 (80) | PAG 1 (2) | | TBA (0.125) | PGMEA (600) | 5.3 | 0.18 | rectangular |
| I-19 | Polymer 19 (80) | PAG 1 (2) | | TBA (0.125) | PGMEA (600) | 5.4 | 0.18 | rectangular |
| I-20 | Polymer 20 (80) | PAG 1 (2) | | TBA (0.125) | PGMEA (600) | 5.6 | 0.18 | rectangular |

TABLE 2

| Example | Base resin | Photoacid generator | Dissolution inhibitor | Basic compound | Solvent | Sensitivity | Resolution | Shape |
|---|---|---|---|---|---|---|---|---|
| I-21 | Polymer 21 (80) | PAG 1 (2) | | TBA (0.125) | PGMEA (600) | 5.3 | 0.15 | rectangular |
| I-22 | Polymer 22 (80) | PAG 1 (2) | | TBA (0.125) | PGMEA (600) | 5.4 | 0.18 | rectangular |
| I-23 | Polymer 23 (80) | PAG 1 (2) | | TBA (0.125) | PGMEA (600) | 5.4 | 0.15 | rectangular |
| I-24 | Polymer 24 (80) | PAG 1 (2) | | TBA (0.125) | PGMEA (600) | 5.5 | 0.18 | rectangular |
| I-25 | Polymer 25 (80) | PAG 1 (2) | | TBA (0.125) | PGMEA (600) | 5.4 | 0.18 | rectangular |
| I-26 | Polymer 26 (80) | PAG 1 (2) | | TBA (0.125) | PGMEA (600) | 5.4 | 0.18 | rectangular |
| I-27 | Polymer 27 | PAG 1 | | TBA | PGMEA | 5.3 | 0.18 | rectangular |

TABLE 2-continued

| Example | Base resin | Photoacid generator | Dissolution inhibitor | Basic compound | Solvent | Sensitivity | Resolution | Shape |
|---|---|---|---|---|---|---|---|---|
| | (80) | (2) | | (0.125) | (600) | | | |
| I-28 | Polymer 28 (80) | PAG 1 (2) | | TBA (0.125) | PGMEA (600) | 5.7 | 0.20 | rectangular |
| I-29 | Polymer 29 (80) | PAG 1 (2) | | TBA (0.125) | PGMEA (600) | 4.8 | 0.18 | rectangular |
| I-30 | Polymer 30 (80) | PAG 1 (2) | | TBA (0.125) | PGMEA (600) | 4.8 | 0.15 | rectangular |
| I-31 | Polymer 31 (80) | PAG 1 (2) | | TBA (0.125) | PGMEA (600) | 4.8 | 0.18 | rectangular |
| I-32 | Polymer 32 (80) | PAG 1 (2) | | TBA (0.125) | PGMEA (600) | 4.7 | 0.18 | rectangular |
| I-33 | Polymer 33 (80) | PAG 1 (2) | | TBA (0.125) | PGMEA (600) | 5.1 | 0.18 | rectangular |
| I-34 | Polymer 34 (80) | PAG 1 (2) | | TBA (0.125) | PGMEA (600) | 5.5 | 0.18 | rectangular |
| I-35 | Polymer 35 (80) | PAG 1 (2) | | TBA (0.125) | PGMEA (600) | 5.0 | 0.18 | rectangular |
| I-36 | Polymer 36 (80) | PAG 1 (2) | | TBA (0.125) | PGMEA (600) | 4.8 | 0.18 | rectangular |
| I-37 | Polymer 37 (80) | PAG 1 (2) | | TBA (0.125) | PGMEA (600) | 5.3 | 0.18 | rectangular |
| I-38 | Polymer 38 (80) | PAG 1 (2) | | TBA (0.125) | PGMEA (600) | 4.8 | 0.18 | rectangular |
| I-39 | Polymer 39 (80) | PAG 1 (2) | | TBA (0.125) | PGMEA (600) | 5.5 | 0.18 | rectangular |
| I-40 | Polymer 40 (80) | PAG 1 (2) | | TBA (0.125) | PGMEA (600) | 5.0 | 0.18 | rectangular |

TABLE 3

| Example | Base resin | Photoacid generator | Dissolution inhibitor | Basic compound | Solvent | Sensitivity | Resolution | Shape |
|---|---|---|---|---|---|---|---|---|
| I-41 | Polymer 1 (80) | PAG 1 (2) | | TEA (0.125) | PG/EL (600) | 5.5 | 0.15 | rectangular |
| I-42 | Polymer 1 (80) | PAG 2 (2) | | TEA (0.125) | PG/EL (600) | 2.7 | 0.15 | rectangular |
| I-43 | Polymer 1 (80) | PAG 3 (2) | | TEA (0.125) | PG/EL (600) | 5.4 | 0.15 | rectangular |
| I-44 | Polymer 1 (80) | PAG 4 (2) | | TEA (0.125) | PG/EL (600) | 5.3 | 0.18 | rectangular |
| I-45 | Polymer 1 (80) | PAG 5 (2) | | TEA (0.125) | PG/EL (600) | 5.2 | 0.18 | rectangular |
| I-46 | Polymer 1 (80) | PAG 6 (2) | | TEA (0.125) | PG/EL (600) | 5.2 | 0.15 | rectangular |
| I-47 | Polymer 1 (80) | PAG 7 (2) | | TEA (0.125) | PG/EL (600) | 3.0 | 0.15 | rectangular |
| I-48 | Polymer 1 (80) | PAG 8 (2) | | TEA (0.125) | PG/EL (600) | 2.3 | 0.15 | rectangular |
| I-49 | Polymer 2 (80) | PAG 8 (2) | | TBA (0.125) | PGMEA (600) | 2.5 | 0.18 | rectangular |
| I-50 | Polymer 2 (80) | PAG 8 (2) | | TEA (0.125) | PGMEA (600) | 2.7 | 0.15 | rectangular |
| I-51 | Polymer 2 (80) | PAG 8 (2) | | TMMEA (0.125) | PGMEA (600) | 2.2 | 0.15 | rectangular |
| I-52 | Polymer 2 (80) | PAG 8 (2) | | TMEMEA (0.125) | PGMEA (600) | 2.0 | 0.15 | rectangular |
| I-53 | Polymer 38 (80) | PAG 8 (2) | | TBA (0.125) | PGMEA (600) | 2.4 | 0.18 | rectangular |
| I-54 | Polymer 38 (80) | PAG 8 (2) | | TEA (0.125) | PGMEA (600) | 2.5 | 0.15 | rectangular |
| I-55 | Polymer 38 (80) | PAG 8 (2) | | TMMEA (0.125) | PGMEA (600) | 2.0 | 0.15 | rectangular |
| I-56 | Polymer 38 (80) | PAG 8 (2) | | TMEMEA (0.125) | PGMEA (600) | 1.8 | 0.18 | rectangular |
| I-57 | Polymer 23 (80) | PAG 8 (2) | DRR 1 (4) | TBA (0.125) | PGMEA (600) | 3.6 | 0.18 | some positive taper |

TABLE 3-continued

| Example | Base resin | Photoacid generator | Dissolution inhibitor | Basic compound | Solvent | Sensitivity | Resolution | Shape |
|---|---|---|---|---|---|---|---|---|
| I-58 | Polymer 23 (80) | PAG 8 (2) | DRR 2 (4) | TBA (0.125) | PGMEA (600) | 2.5 | 0.18 | some positive taper |
| I-59 | Polymer 23 (80) | PAG 8 (2) | DRR 3 (4) | TBA (0.125) | PGMEA (600) | 3.5 | 0.18 | some positive taper |
| I-60 | Polymer 23 (80) | PAG 8 (2) | DRR 4 (4) | TBA (0.125) | PGMEA (600) | 2.9 | 0.15 | rectangular |

TABLE 4

| Example | Base resin | Photoacid generator | Dissolution inhibitor | Basic compound | Solvent | Sensitivity | Resolution | Shape |
|---|---|---|---|---|---|---|---|---|
| I-61 | Polymer 34 (80) | PAG 2 (1) PAG 8 (1) | | TBA (0.125) | PGMEA (600) | 2.6 | 0.15 | rectangular |
| I-62 | Polymer 35 (80) | PAG 2 (1) PAG 8 (1) | | TBA (0.125) | PGMEA (600) | 2.2 | 0.15 | rectangular |
| I-63 | Polymer 34 (80) | PAG 8 (2) | ACC 1 (6) | TBA (0.125) | PGMEA (600) | 2.4 | 0.18 | rectangular |
| I-64 | Polymer 35 (80) | PAG 8 (2) | ACC 1 (6) | TBA (0.125) | PGMEA (600) | 2.1 | 0.18 | rectangular |
| I-65 | Polymer 2 (40) Polymer 29 (40) | PAG 8 (2) | | TEA (0.125) | PGMEA (600) | 2.3 | 0.15 | rectangular |
| I-66 | Polymer 2 (40) Polymer 31 (40) | PAG 8 (2) | | TEA (0.125) | PGMEA (600) | 2.1 | 0.15 | rectangular |
| I-67 | Polymer 1 (40) Polymer 57 (40) | PAG 8 (2) | | TEA (0.125) | PGMEA (600) | 2.6 | 0.15 | rectangular |
| I-68 | Polymer 23 (40) Polymer 57 (40) | PAG 8 (2) | | TEA (0.125) | PGMEA (600) | 2.5 | 0.15 | rectangular |
| I-69 | Polymer 1 (40) Polymer 58 (40) | PAG 8 (2) | | TEA (0.125) | PGMEA (600) | 3.4 | 0.15 | rectangular |
| I-70 | Polymer 23 (40) Polymer 58 (40) | PAG 8 (2) | | TEA (0.125) | PGMEA (600) | 3.5 | 0.15 | rectangular |

TABLE 5

| Example | Base resin | Photoacid generator | Dissolution inhibitor | Basic compound | Solvent | Sensitivity | Resolution | Shape |
|---|---|---|---|---|---|---|---|---|
| I-71 | Polymer 1 (40) Polymer 59 (40) | PAG 8 (2) | | TEA (0.125) | PGMEA (600) | 3.0 | 0.15 | rectangular |
| I-72 | Polymer 23 (40) Polymer 59 (40) | PAG 8 (1) | | TEA (0.125) | PGMEA (600) | 3.1 | 0.15 | rectangular |

TABLE 5-continued

| Example | Base resin | Photoacid generator | Dissolution inhibitor | Basic compound | Solvent | Sensitivity | Resolution | Shape |
|---|---|---|---|---|---|---|---|---|
| I-73 | Polymer 1 (40) Polymer 60 (40) | PAG 8 (2) | | TEA (0.125) | PGMEA (600) | 3.8 | 0.18 | rectangular |
| I-74 | Polymer 23 (40) Polymer 60 (40) | PAG 8 (2) | | TEA (0.125) | PGMEA (600) | 2.8 | 0.18 | rectangular |
| I-75 | Polymer 1 (40) Polymer 61 (40) | PAG 8 (2) | | TEA (0.125) | PGMEA (600) | 2.8 | 0.18 | rectangular |
| I-76 | Polymer 23 (40) Polymer 61 (40) | PAG 8 (2) | | TEA (0.125) | PGMEA (600) | 2.7 | 0.18 | rectangular |
| I-77 | Polymer 1 (40) Polymer 62 (40) | PAG 8 (2) | | TEA (0.125) | PGMEA (600) | 2.9 | 0.18 | rectangular |
| I-78 | Polymer 23 (40) Polymer 62 (40) | PAG 8 (2) | | TEA (0.125) | PGMEA (600) | 3.0 | 0.18 | rectangular |
| I-79 | Polymer 1 (40) Polymer 63 (40) | PAG 8 (2) | | TEA (0.125) | PGMEA (600) | 3.1 | 0.20 | rectangular |
| I-80 | Polymer 1 (40) Polymer 64 (40) | PAG 8 (2) | | TEA (0.125) | PGMEA (600) | 3.0 | 0.20 | rectangular |

Comparative Example I

Polymers 65 to 72 shown by the chemical formulae below were formulated into resist compositions, which were examined for resolution.

Comparative Examples I-1 to I-8: Evaluation of resist resolution

Resist compositions were similarly prepared using Polymers 65 to 72 and tested as in Example I.

The composition and test results of the resist materials are shown in Table 6.

(Polymer 65)

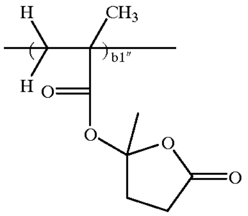

-continued

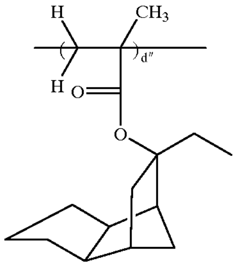

(b1″ = 0.30, d″ = 0.70, Mw = 11,500)

(Polymer 66)

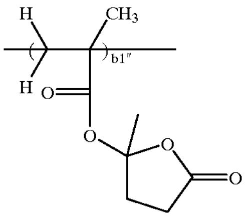

-continued
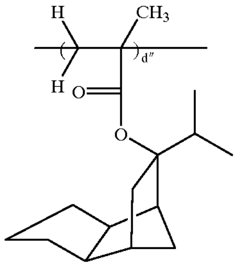
(b1″ = 0.30, d″ = 0.70, Mw = 11,900)
(Polymer 67)
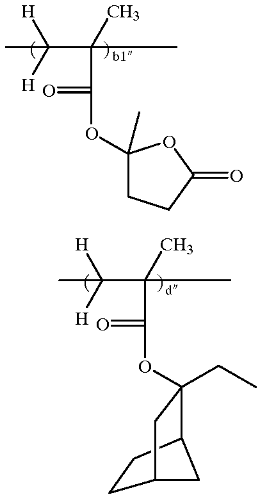
(b1″ = 0.30, d″ = 0.70, Mw = 10,100)
(Polymer 68)
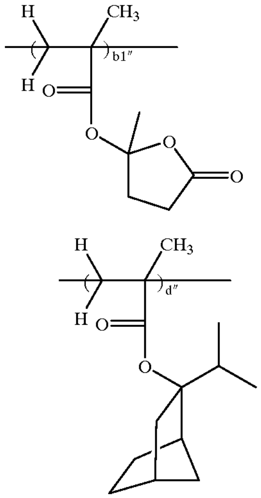
(b1″ = 0.30, d″ = 0.70, Mw = 10,500)
-continued
(Polymer 69)
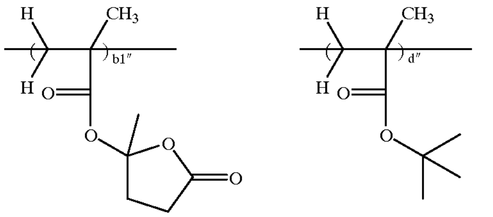
(b1″ = 0.30, d″ = 0.70, Mw = 7,700)
(Polymer 70)
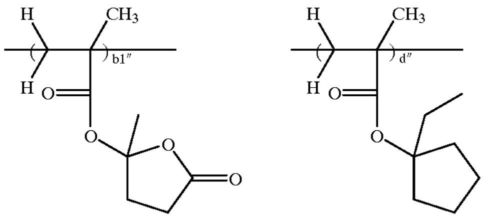
(b1″ = 0.30, d″ = 0.70, Mw = 9,100)
(Polymer 71)
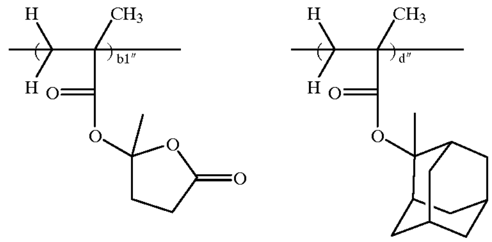
(b1″ = 0.30, d″ = 0.70, Mw = 11,000)
(Polymer 72)
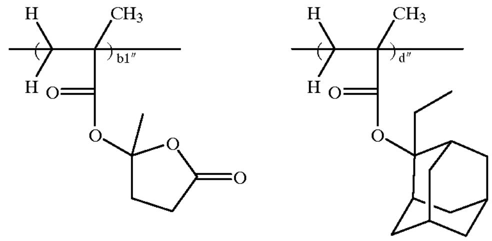
(b1″ = 0.30, d″ = 0.70, Mw = 11,500)

TABLE 6

| Comparative Example | Base resin | Photoacid generator | Dissolution inhibitor | Basic compound | Solvent | Sensitivity | Resolution | Shape |
|---|---|---|---|---|---|---|---|---|
| I-1 | Polymer 65 (80) | PAG 1 (2) | | TBA (0.125) | PGMEA (600) | 14.5 | 0.20 | rectangular |
| I-2 | Polymer 66 (80) | PAG 1 (2) | | TBA (0.125) | PGMEA (600) | 13.8 | 0.20 | rectangular |
| I-3 | Polymer 67 (80) | PAG 1 (2) | | TBA (0.125) | PGMEA (600) | 14.7 | 0.20 | rectangular |
| I-4 | Polymer 68 (80) | PAG 1 (2) | | TBA (0.125) | PGMEA (600) | 14.0 | 0.20 | rectangular |
| I-5 | Polymer 69 (80) | PAG 1 (2) | | TBA (0.125) | PGMEA (600) | 13.3 | 0.20 | rectangular |
| I-6 | Polymer 70 (80) | PAG 1 (2) | | TBA (0.125) | PGMEA (600) | 7.5 | 0.18 | rectangular |
| I-7 | Polymer 71 (80) | PAG 1 (2) | | TBA (0.125) | PGMEA (600) | 12.5 | 0.20 | rectangular |
| I-8 | Polymer 72 (80) | PAG 1 (2) | | TBA (0.125) | PGMEA (600) | 11.7 | 0.20 | rectangular |

It is seen from Tables 1 to 6 that the exo-form 2-alkylbicyclo[2.2.1]heptan-2-yl ester sites within the scope of the invention are highly reactive as compared with endo-form isomers and prior art acid-decomposing sites and ensure that resist materials have a higher sensitivity and resolution than prior art resist materials.

Example II

Polymers 1 to 40 obtained in the above Synthetic Examples were examined for etching resistance.

Examples II-1 to II-40: Evaluation of polymers' etching resistance

Each of Polymers 1 to 40 obtained in Synthetic Examples and a comparative polymer (polymethyl methacrylate, molecular weight 10,000) was dissolved in cyclohexanone, and spin coated onto a silicon wafer to a thickness of 1.0 μm. The coating was baked on a hot plate at 110° C. for 90 seconds. These coatings were etched with a chlorine-base gas or a fluorine-base gas while the etching rate (Å/min) was measured.

The results are shown in Tables 7 and 8 while the settings of the instrument are shown in Table 9.

TABLE 7

| Example | Resin | Solvent | Chlorine etching | Fluorine etching |
|---|---|---|---|---|
| II-1 | Polymer 1 (80) | cyclohexanone (480) | 1560 | 1680 |
| II-2 | Polymer 2 (80) | cyclohexanone (480) | 1540 | 1660 |
| II-3 | Polymer 3 (80) | cyclohexanone (480) | 1600 | 1700 |
| II-4 | Polymer 4 (80) | cyclohexanone (480) | 1660 | 1740 |
| II-5 | Polymer 5 (80) | cyclohexanone (480) | 1640 | 1720 |
| II-6 | Polymer 6 (80) | cyclohexanone (480) | 1700 | 1760 |
| II-7 | Polymer 7 (80) | cyclohexanone (480) | 1600 | 1700 |
| II-8 | Polymer 8 (80) | cyclohexanone (480) | 1560 | 1680 |
| II-9 | Polymer 9 (80) | cyclohexanone (480) | 1540 | 1660 |
| II-10 | Polymer 10 (80) | cyclohexanone (480) | 1800 | 1840 |
| II-11 | Polymer 11 (80) | cyclohexanone (480) | 1720 | 1780 |
| II-12 | Polymer 12 (80) | cyclohexanone (480) | 1780 | 1820 |
| II-13 | Polymer 13 (80) | cyclohexanone (480) | 1640 | 1720 |
| II-14 | Polymer 14 (80) | cyclohexanone (480) | 1580 | 1700 |
| II-15 | Polymer 15 (80) | cyclohexanone (480) | 1580 | 1700 |
| II-16 | Polymer 16 (80) | cyclohexanone (480) | 1760 | 1800 |
| II-17 | Polymer 17 (80) | cyclohexanone (480) | 1760 | 1800 |
| II-18 | Polymer 18 (80) | cyclohexanone (480) | 1520 | 1640 |
| II-19 | Polymer 19 (80) | cyclohexanone (480) | 1640 | 1720 |
| II-20 | Polymer 20 (80) | cyclohexanone (480) | 1620 | 1720 |
| II-21 | Polymer 21 (80) | cyclohexanone (480) | 1620 | 1720 |

TABLE 7-continued

| Example | Resin | Solvent | Chlorine etching | Fluorine etching |
|---|---|---|---|---|
| II-22 | Polymer 22 (80) | cyclohexanone (480) | 1680 | 1760 |
| II-23 | Polymer 23 (80) | cyclohexanone (480) | 1620 | 1720 |
| II-24 | Polymer 24 (80) | cyclohexanone (480) | 1760 | 1800 |
| II-25 | Polymer 25 (80) | cyclohexanone (480) | 1820 | 1840 |
| II-26 | Polymer 26 (80) | cyclohexanone (480) | 1780 | 1820 |
| II-27 | Polymer 27 (80) | cyclohexanone (480) | 1760 | 1800 |
| II-28 | Polymer 28 (80) | cyclohexanone (480) | 1800 | 1820 |
| II-29 | Polymer 29 (80) | cyclohexanone (480) | 1460 | 1600 |
| II-30 | Polymer 30 (80) | cyclohexanone (480) | 1520 | 1640 |

TABLE 8

| Example | Resin | Solvent | Chlorine etching | Fluorine etching |
|---|---|---|---|---|
| II-31 | Polymer 31 (80) | cyclohexanone (480) | 1500 | 1640 |
| II-32 | Polymer 32 (80) | cyclohexanone (480) | 1500 | 1620 |
| II-33 | Polymer 33 (80) | cyclohexanone (480) | 1500 | 1620 |
| II-34 | Polymer 34 (80) | cyclohexanone (480) | 1780 | 1820 |
| II-35 | Polymer 35 (80) | cyclohexanone (480) | 1800 | 1840 |
| II-36 | Polymer 36 (80) | cyclohexanone (480) | 1820 | 1840 |
| II-37 | Polymer 37 (80) | cyclohexanone (480) | 1660 | 1680 |
| II-38 | Polymer 38 (80) | cyclohexanone (480) | 1660 | 1680 |
| II-39 | Polymer 39 (80) | cyclohexanone (480) | 1700 | 1720 |
| II-40 | Polymer 40 (80) | cyclohexanone (480) | 1680 | 1700 |
| Comparative Example | polymethyl methacrylate (80) | cyclohexanone (480) | 2500 | 2250 |

TABLE 9

Settings of the instrument

| | Chlorine etching | Fluorine etching |
|---|---|---|
| Manufacturer | Nichiden Anerba K.K. | Tokyo Electron K.K. |
| Model | L451D | TE8500 |
| Gas/flow rate | $Cl_2$/20 sccm | $CHF_3$/7 sccm |
| | $O_2$/2 sccm | $CF_4$/45 sccm |
| | $CHF_3$/15 sccm | $O_2$/20 sccm |
| | $BCl_3$/100 sccm | Ar/90 sccm |
| RF power | 300 W | 600 W |

TABLE 9-continued

| | Settings of the instrument | |
|---|---|---|
| | Chlorine etching | Fluorine etching |
| Pressure | 2 Pa | 60 Pa |
| Temperature | 23° C. | −20° C. |
| Time | 360 sec | 60 sec |

It is seen from Tables 7 and 8 that the polymers within the scope of the invention are highly resistant to etching.

Example III

Resist compositions were formulated using Polymers 41 to 56 obtained in the above Synthetic Examples and examined for resolution.

Examples III-1 to III-40: Evaluation of resist resolution

Resist compositions were prepared by using Polymers 41 to 56 or Polymers 73 to 76 shown below as the base resin, and dissolving the polymer, a photoacid generator (designated as PAG 1 to 8), a dissolution inhibitor (designated as DRR1 to 4), a basic compound, and a compound having a ≡C—COOH group in the molecule (ACC 1 and 2) in a solvent containing 0.05% by weight of surfactant Florade FC-430 (Sumitomo 3M) in the combination shown in the following Tables. These compositions were each filtered through a 0.2 $\mu$m Teflon filter, thereby giving resist solutions.

(Polymer 73)

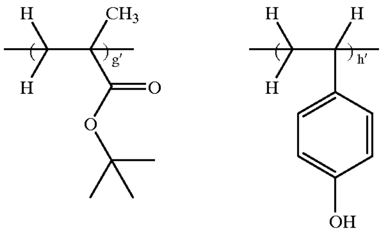

(g′ = 0.35, h′ = 0.65, Mw = 9,600)

(Polymer 74)

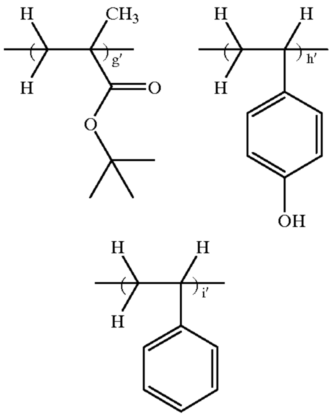

(g′ = 0.40, h′ = 0.40, i′ = 0.20, Mw = 9,400)

-continued (Polymer 75)

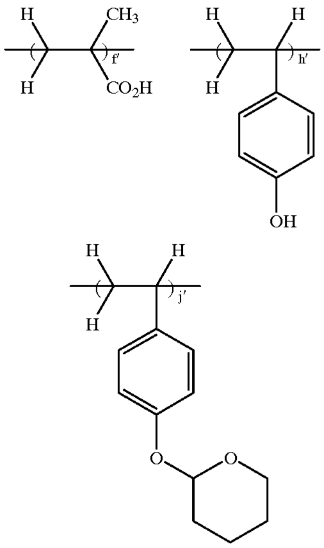

(f′ = 0.05, h′ = 0.55, j′ = 0.40, Mw = 11,400)

(Polymer 76)

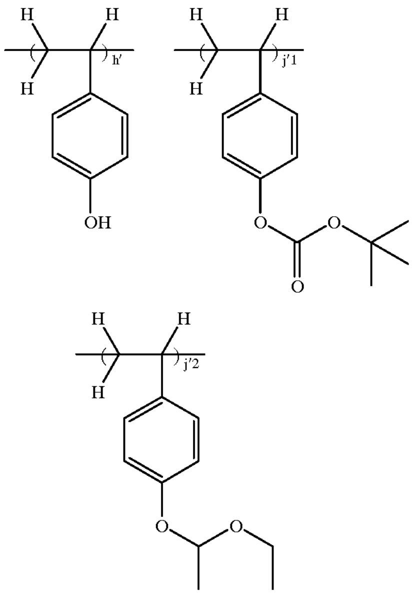

(h′ = 0.65, j′1 = 0.15, j′2 = 0.20, Mw = 11,200)

(ACC 1)

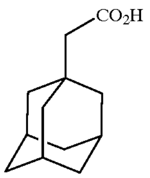

(ACC 2)

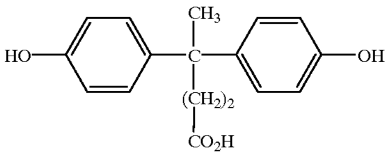

These resist solutions were spin-coated onto silicon wafers, then baked at 100° C. for 90 seconds on a hot plate to give resist films having a thickness of 0.7 μm. The resist films were exposed using an KrF excimer laser stepper (Nikon Corporation; NA 0.5), then baked (PEB) at 110° C. for 90 seconds, and developed with a solution of 2.38% tetramethylammonium hydroxide in water, thereby giving positive patterns.

The resulting resist patterns were evaluated as described below.

First, the sensitivity (Eth, $mJ/cm^2$) was determined. Next, the optimal dose (sensitivity Eop, $mJ/cm^2$) was defined as the dose which provides a 1:1 resolution at the top and bottom of a 0.30 μm line-and-space pattern, and the resolution of the resist under evaluation was defined as the minimum line width (μm) of the liners and spaces that separated at this dose. The shape of the resolved resist pattern was examined under a scanning electron microscope.

The composition and test results of the resist materials are shown in Tables 10 and 11.

TABLE 10

| Example | Base resin | Photoacid generator | Dissolution inhibitor | Basic compound | Solvent | Sensitivity | Resolution | Shape |
|---|---|---|---|---|---|---|---|---|
| III-1 | Polymer 41 (80) | PAG 1 (2) | | TBA (0.125) | PGMEA (600) | 11.0 | 0.22 | rectangular |
| III-2 | Polymer 42 (80) | PAG 1 (2) | | TBA (0.125) | PGMEA (600) | 12.2 | 0.22 | rectangular |
| III-3 | Polymer 43 (80) | PAG 1 (2) | | TBA (0.125) | PGMEA (600) | 10.1 | 0.22 | rectangular |
| III-4 | Polymer 44 (80) | PAG 1 (2) | | TBA (0.125) | PGMEA (600) | 10.7 | 0.22 | rectangular |
| III-5 | Polymer 45 (80) | PAG 1 (2) | | TBA (0.125) | PGMEA (600) | 10.6 | 0.22 | rectangular |
| III-6 | Polymer 46 (80) | PAG 1 (2) | | TBA (0.125) | PGMEA (600) | 11.1 | 0.24 | rectangular |
| III-7 | Polymer 47 (80) | PAG 1 (2) | | TBA (0.125) | PGMEA (600) | 10.8 | 0.22 | rectangular |
| III-8 | Polymer 48 (80) | PAG 1 (2) | | TBA (0.125) | PGMEA (600) | 10.9 | 0.24 | rectangular |
| III-9 | Polymer 49 (80) | PAG 1 (2) | | TBA (0.125) | PGMEA (600) | 12.0 | 0.22 | rectangular |
| III-10 | Polymer 50 (80) | PAG 1 (2) | | TBA (0.125) | PGMEA (600) | 12.4 | 0.22 | rectangular |
| III-11 | Polymer 51 (80) | PAG 1 (2) | | TBA (0.125) | PGMEA (600) | 12.5 | 0.24 | rectangular |
| III-12 | Polymer 52 (80) | PAG 1 (2) | | TBA (0.125) | PGMEA (600) | 12.4 | 0.24 | rectangular |
| III-13 | Polymer 53 (80) | PAG 1 (2) | | TBA (0.125) | PGMEA (600) | 10.8 | 0.24 | rectangular |
| III-14 | Polymer 54 (80) | PAG 1 (2) | | TBA (0.125) | PGMEA (600) | 10.6 | 0.22 | rectangular |
| III-15 | Polymer 55 (80) | PAG 1 (2) | | TBA (0.125) | PGMEA (600) | 10.9 | 0.24 | rectangular |
| III-16 | Polymer 56 (80) | PAG 1 (2) | | TBA (0.125) | PGMEA (600) | 10.5 | 0.22 | rectangular |
| III-17 | Polymer 47 (80) | PAG 1 (2) | | TEA (0.125) | PG/EL (600) | 11.5 | 0.22 | rectangular |
| III-18 | Polymer 47 (80) | PAG 2 (2) | | TEA (0.125) | PG/EL (600) | 6.7 | 0.22 | rectangular |
| III-19 | Polymer 47 (80) | PAG 3 (2) | | TEA (0.125) | PG/EL (600) | 11.3 | 0.22 | rectangular |
| III-20 | Polymer 47 (80) | PAG 4 (2) | | TEA (0.125) | PG/EL (600) | 11.0 | 0.22 | rectangular |
| III-21 | Polymer 47 (80) | PAG 5 (2) | | TEA (0.125) | PG/EL (600) | 10.5 | 0.22 | rectangular |
| III-22 | Polymer 47 (80) | PAG 6 (2) | | TEA (0.125) | PG/EL (600) | 10.7 | 0.22 | rectangular |
| III-23 | Polymer 47 (80) | PAG 7 (2) | | TEA (0.125) | PG/EL (600) | 7.3 | 0.22 | rectangular |
| III-24 | Polymer 47 (80) | PAG 8 (2) | | TEA (0.132) | PG/EL (600) | 6.5 | 0.22 | rectangular |
| III-25 | Polymer 48 (80) | PAG 2 (2) | | TBA (0.125) | PGMEA (600) | 6.7 | 0.22 | rectangular |
| III-26 | Polymer 48 (80) | PAG 2 (2) | | TEA (0.125) | PGMEA (600) | 6.5 | 0.22 | rectangular |
| III-27 | Polymer 48 (80) | PAG 2 (2) | | TMMEA (0.125) | PGMEA (600) | 6.2 | 0.22 | rectangular |
| III-28 | Polymer 48 (80) | PAG 2 (2) | | TMEMEA (0.125) | PGMEA (600) | 6.0 | 0.22 | rectangular |
| III-29 | Polymer 49 (80) | PAG 1 (2) | DRR 1 (4) | TEA (0.125) | PGMEA (600) | 11.7 | 0.22 | rectangular |
| III-30 | Polymer 49 (80) | PAG 1 (2) | DRR 2 (4) | TEA (0.125) | PGMEA (600) | 11.6 | 0.22 | rectangular |

TABLE 10-continued

| Example | Base resin | Photoacid generator | Dissolution inhibitor | Basic compound | Solvent | Sensitivity | Resolution | Shape |
|---|---|---|---|---|---|---|---|---|
| III-31 | Polymer 49 (80) | PAG 1 (2) | DRR 3 (4) | TEA (0.125) | PGMEA (600) | 11.4 | 0.20 | rectangular |

TABLE 11

| Example | Base resin | Photoacid generator | Dissolution inhibitor | Basic compound | Solvent | Sensitivity | Resolution | Shape |
|---|---|---|---|---|---|---|---|---|
| III-32 | Polymer 49 (80) | PAG 1 (2) | DRR 4 (4) | TEA (0.125) | PGMEA (600) | 11.3 | 0.20 | rectangular |
| III-33 | Polymer 51 (80) | PAG 1 (2) | ACC 1 (6) | TEA (0.125) | PGMEA (600) | 10.2 | 0.20 | rectangular |
| III-34 | Polymer 51 (80) | PAG 1 (2) | ACC 2 (6) | TEA (0.125) | PGMEA (600) | 10.4 | 0.20 | rectangular |
| III-35 | Polymer 54 (80) | PAG 1 (1) PAG 6 (1) | | TBA (0.125) | PGMEA (600) | 10.3 | 0.20 | rectangular |
| III-36 | Polymer 55 (80) | PAG 1 (1) PAG 6 (1) | | TBA (0.125) | PGMEA (600) | 10.0 | 0.20 | rectangular |
| III-37 | Polymer 47 (40) Polymer 73 (40) | PAG 7 (2) | | TBA (0.125) | PGMEA (600) | 7.7 | 0.22 | rectangular |
| III-38 | Polymer 47 (40) Polymer 74 (40) | PAG 7 (2) | | TBA (0.125) | PGMEA (600) | 7.5 | 0.22 | rectangular |
| III-39 | Polymer 47 (40) Polymer 75 (40) | PAG 7 (2) | | TBA (0.125) | PGMEA (600) | 6.5 | 0.22 | rectangular |
| III-40 | Polymer 47 (40) Polymer 76 (40) | PAG 7 (2) | | TBA (0.125) | PGMEA (600) | 6.9 | 0.22 | rectangular |

Comparative Example II

Polymers 73 to 76 shown by the chemical formulae above were formulated into resist compositions, which were examined for resolution.

TABLE 12

| Comparative Example | Base resin | Photoacid generator | Dissolution inhibitor | Basic compound | Solvent | Sensitivity | Resolution | Shape |
|---|---|---|---|---|---|---|---|---|
| II-1 | Polymer 73 (80) | PAG 1 (2) | | TEA (0.125) | PGMEA (600) | 16.5 | 0.26 | T-top |
| II-2 | Polymer 74 (80) | PAG 1 (2) | | TEA (0.125) | PGMEA (600) | 16.4 | 0.26 | T-top |
| II-3 | Polymer 75 (80) | PAG 1 (2) | | TEA (0.125) | PGMEA (600) | 6.5 | 0.28 | thinning |
| II-4 | Polymer 76 (80) | PAG 1 (2) | | TEA (0.125) | PGMEA (600) | 15.4 | 0.26 | T-top |

Comparative Examples II-1 to II-4: Evaluation of resist resolution

Resist compositions were similarly prepared using Polymers 73 to 76 and tested as in Example III.

The composition and test results of the resist materials are shown in Table 12.

It is seen from Tables 10 to 12 that the exo-form 2-alkylbicyclo[2.2.]heptan-2-yl ester sites within the scope of the invention are highly reactive as compared with prior art acid-decomposing sites and ensure that resist materials have a higher sensitivity and resolution than prior art resist materials.

Japanese Patent Application Nos. 10-312533 and 11-075355 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An ester compound of the following general formula (1):

(1)

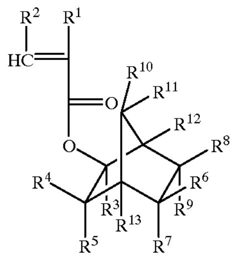

wherein $R^1$ is hydrogen, methyl or $CH_2CO_2R^{14}$;

$R^2$ is hydrogen, methyl or $CO_2R^{14}$;

$R^3$ is a straight, branched or cyclic alkyl group of 1 to 8 carbon atoms;

$R^4$, $R^5$ and $R^{10}$ to $R^{13}$ each are hydrogen;

$R^6$ to $R^9$ are each hydrogen or $R^6$ and $R^8$ or $R^7$ and $R^9$ form a cyclopentane ring or a bicyclo[2.2.1 ]heptane ring; and $R^{14}$ is a straight, branched or cyclic alkyl of 1 to 15 carbon atoms, with the proviso that the formula also represents an enantiomer.

2. A compound according to claim 1, wherein $R^3$ is methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, and cyclohexylethyl.

3. A compound according to claim 1, wherein $R^{14}$ is methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, and butyladamantyl.

4. A polymer comprising units of an ester compound of the following general formula (1a):

(1a)

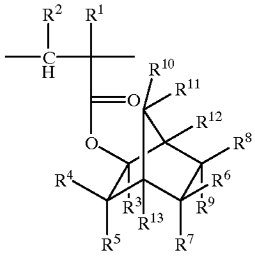

wherein $R^1$ is hydrogen, methyl or $CH_2CO_2R^{14}$;

$R^2$ is hydrogen, methyl or $CO_2R^{14}$;

$R^3$ is a straight, branched or cyclic alkyl group of 1 to 8 carbon atoms;

$R^4$, $R^5$ and $R^{10}$ to $R^{13}$ each are hydrogen;

$R^6$ to $R^9$ are each hydrogen or $R^6$ and $R^8$ or $R^7$ and $R^9$ form a cyclopentane ring or a bicyclo[2.2.1]heptane ring; and $R^{14}$ is a straight, branched or cyclic alkyl of 1 to 15 carbon atoms, with the proviso that the formula also represents an enantiomer, said polymer having a weight average molecular weight of 1,000 to 500,000.

5. The polymer of claim 4 comprising recurring units of at least one of the following formulae (2a) to (13a):

(2a)

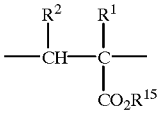

(3a)

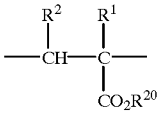

(4a)

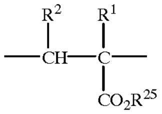

(5a)

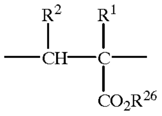

(6a)

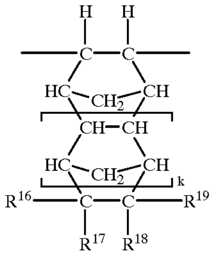

(7a)

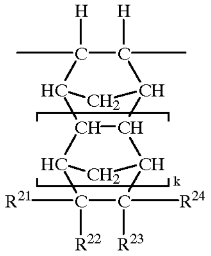

-continued (8a)

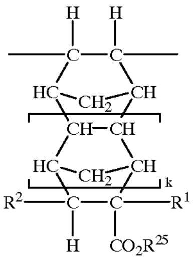

(9a)

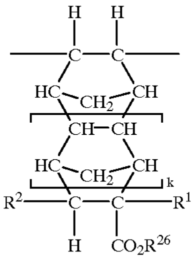

(10a)

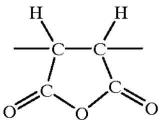

(11a)

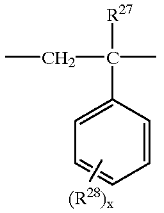

(12a)

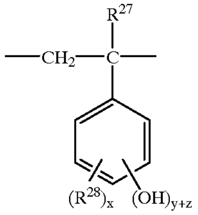

(13a)

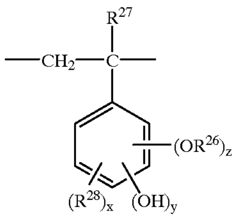

wherein $R^{15}$ is hydrogen or a monovalent hydrocarbon group of 1 to 15 carbon atoms containing a carboxyl or hydroxyl group; at least one of $R^{16}$ to $R^{19}$ represents a monovalent hydrocarbon group of 1 to 15 carbon atoms containing a carboxyl or hydroxyl group, and the remaining of $R^{16}$ to $R^{19}$ independently represent hydrogen or a straight, branched or cyclic alkyl group of 1 to 15 carbon atoms, or $R^{16}$ to $R^{19}$, taken together, may form a ring with the proviso that at least one of $R^{16}$ to $R^{19}$ represents a divalent hydrocarbon group of 1 to 15 carbon atoms containing a carboxyl or hydroxyl group, and the remaining of $R^{16}$ to $R^{19}$ independently represent a straight, branched or cyclic alkylene group of 1 to 15 carbon atoms; $R^{20}$ is a monovalent hydrocarbon group of 3 to 15 carbon atoms containing a —$CO_2$— partial structure; at least one of $R^{21}$ to $R^{24}$ represents a monovalent hydrocarbon group of 2 to 15 carbon atoms containing a —$CO_2$— partial structure, and the remaining of $R^{21}$ to $R^{24}$ independently represent hydrogen or a straight, branched or cyclic alkyl group of 1 to 15 carbon atoms, or $R^{21}$ to $R^{24}$, taken together, may form a ring with the proviso that at least one of $R^{21}$ to $R^{24}$ represents a divalent hydrocarbon group of 1 to 15 carbon atoms containing a —$CO_2$— partial structure, and the remaining of $R^{21}$ to $R^{24}$ independently represent a straight, branched or cyclic alkylene group of 1 to 15 carbon atoms; $R^{25}$ is a polycyclic hydrocarbon group of 7 to 15 carbon atoms or an alkyl group containing a polycyclic hydrocarbon group; $R^{26}$ is an acid labile group; $R^{27}$ is hydrogen or methyl; $R^{28}$ is a straight, branched or cyclic alkyl group of 1 to 8 carbon atoms; k is equal to 0 or 1, and x, y and z are integers of 0 to 3, satisfying $x+y+z \leqq 5$ and $1 \leqq y+z$.

6. A polymer according to claim 5, wherein $R^{15}$ is carboxyethyl, carboxybutyl, carboxycyclopentyl, carboxycyclohexyl, carboxynorbornyl, carboxyadamantyl, hydroxyethyl, hydroxybutyl, hydroxycyclopentyl, hydroxycyclohexyl, hydroxynorbornyl, or hydroxyadamantyl.

7. A polymer according to claim 5, wherein at least one of $R^{16}$ to $R^{19}$ is carboxy, carboxymethyl, carboxyethyl, carboxybutyl, hydroxymethyl, hydroxyethyl, hydroxybutyl, 2-carboxyethoxycarbonyl, 4-carboxybutoxycarbonyl, 2-hydroxyethoxycarbonyl, 4-hydroxybutoxycarbonyl, carboxycyclopentyloxycarbonyl, carboxycyclohexyloxycarbonyl, carboxynorbomnyloxycarbonyl, carboxyadamantyloxycarbonyl, hydroxycyclopentyloxycarbonyl, hydroxycyclohexyloxycarbonyl, hydroxynorbornyloxycarbonyl, and hydroxyadamantyloxycarbonyl.

8. A polymer according to claim 5, wherein $R^{20}$ is 2-oxooxolan-3-yl, 4,4-dimethyl-2-oxooxolan-3-yl, 4-methyl-2-oxooxan-4-yl, 2-oxo-1,3-dioxolan-4-ylmethyl, and 5-methyl-2-oxooxolan-5-yl.

9. A polymer according to claim 5, wherein at least one of $R^{21}$ to $R^{24}$ is 2-oxooxolan-3-yloxycarbonyl, 4,4-dimethyl-2-oxooxolan-3-yloxycarbonyl, 4-methyl-2-oxooxan-4-yloxycarbonyl, 2-oxo-13-dioxolan-4-ylmethyloxycarbonyl, and 5-methyl-2-oxooxolan-5-yloxy-carbonyl.

10. A polymer according to claim 5, wherein $R^{25}$ is norbomyl, bicyclo[3.3.1]-nonyl, tricyclo[5.2.1.$0^{2,6}$]decyl, adamantyl, ethyladamantyl, butyladamantyl, norbomylmethyl, and adamantylmethyl.

11. A polymer according to claim 5, wherein $R^{26}$ is a tertiary alkyl group of 4–20 carbon atoms, a trialkylsilyl group in which the alkyl groups have 1–6 carbon atoms, an oxoalkyl group of 4–20 carbon atoms, or a group of the following formula (14) and (15):

(14)

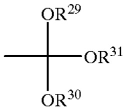

(15)

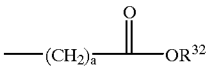

wherein $R^{29}$ and $R^{30}$ are each independently hydrogen or a straight, branched or cyclic alkyl group of 1–18 carbon atoms, $R^{31}$ is a monovalent hydrocarbon of 1–18 carbon atoms which may have a heteroatom which may be straight branched or cyclic, and in which some hydrogen atoms may be replaced by hydroxyl alkoxy, oxo, amino or alkylamino groups.

$R^{29}$ and $R^{30}$ or $R^{29}$ and $R^{31}$ or $R^{30}$ and $R^{31}$, taken together, may each also form a ring, wherein each of $R^{29}$, $R^{30}$ and $R^{31}$ demonstrate a straight or branched alkylene group of 1–18 carbon atoms; and $R^{32}$ is a tertiary alkyl group of 4–20 C atoms, a trialkylsilyl group in which the alkyls have 1–6 carbon atoms, an oxoalkyl group of 4–20 carbon atoms, or as a group of formula (14), and a is an integer of 0 to 6.

12. A polymer according to claim 5, wherein $R^{15}$ is carboxyethyl, carboxybutyl, carboxycyclopentyl, carboxycyclohexyl, carboxynorbornyl, carboxyadamantyl, hydroxyethyl, hydroxybutyl, hydroxycyclopentyl, hydroxycyclohexyl, hydioxynorbornyl, or hydroxyadamantyl;

at least one of $R^{16}$ to $R^{19}$ is carboxy, carboxymethyl, carboxyethyl, carboxybutyl, hydroxymethyl, hydroxyethyl, hydroxybutyl, 2-carboxyethoxycarbonyl, 4-carboxybutoxycarbonyl, 2-hydroxyethoxycarbonyl, 4-hydroxybutoxycarbonyl, carboxycyclopentyloxycarbonyl, carboxycyclohexyloxycarbonyl, carboxynorbornyloxycarbonyl, carboxyadamantyloxycarbonyl, hydroxycyclopentyloxycarbonyl, hydroxycyclohexyloxycarbonyl, hydroxynorbornyloxycarbonyl, and hydroxyadamantyloxycarbonyl;

$R^{20}$ is 2-oxooxolan-3-yl, 4,4-dimethyl-2-oxooxolan-3-yl, 4-methyl-2-oxooxan-4-yl, 2-oxo-1,3-dioxolan-4-ylmethyl, and 5-methyl-2-oxooxolan-5-yl;

at least one of $R^{21}$ to $R^{24}$ is 2-oxooxolan-3-yloxycarbonyl, 4,4-dimethyl-2-oxooxolan-3-yloxycarbonyl, 4-methyl-2-oxooxan-4-yloxycarbonyl, 2-oxo-13 -dioxolan-4-ylmethyloxycarbonyl, and 5-methyl-2-oxooxolan-5-yloxy-carbonyl;

$R^{25}$ is norbornyl, bicyclo[3.3.1 ]-nonyl, tricyclo[5.2.1.$0^{2,6}$]decyl, adamantyl, ethyladamantyl, butyladamantyl, norbomylmethyl, and adamantylmethyl;

$R^{26}$ is a tertiary alkyl group of 4–20 carbon atoms, a trialkylsilyl group in which the alkyl groups have 1–6 carbon atoms, an oxoalkyl group of 4–20 carbon atoms, or a group of the following formula (14) and (15):

(14)

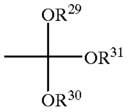

(15)

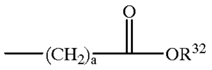

wherein $R^{29}$ and $R^{30}$ are each independently hydrogen or a straight, branched or cyclic alkyl group of 1–18 carbon atoms, $R^{31}$ is a monovalent hydrocarbon of 1–18 carbon atoms which may have a heteroatom which may be straight branched or cyclic, and in which some hydrogen atoms may be replaced by hydroxyl, alkoxy, oxo, amino or alkylamino groups.

$R^{29}$ and $R^{30}$ or $R^{29}$ and $R^{31}$ or $R^{30}$ and $R^{31}$, taken together, may each also form a ring, wherein each of $R^{29}$, $R^{30}$ and $R^{31}$ demonstrate a straight or branched alkylene group of 1–18 carbon atoms; and $R^{32}$ is a tertiary alkyl group of 4–20 C atoms, a trialkylsilyl group in which the alkyls have 1–6 carbon atoms, an oxoalkyl group of 4–20 carbon atoms, or as a group of formula (14), and a is an integer of 0 to 6.

13. A polymer according to claim 4, wherein said polymer has a weight average molecular weight of 5000 to 100,000.

14. A method for preparing a polymer comprising effecting radical polymerization, anionic polymerization or coordination polymerization between an ester compound of formula (1) and another compound having a carbon-to-carbon double bond.

15. A resist composition comprising the polymer of claim 4.

16. A resist composition comprising the polymer of claim 4, a photoacid generator, and an organic solvent.

17. A method for forming a pattern, comprising the steps of:

applying the resist composition of claim 15 onto a substrate to form a coating, heat treating the coating and exposing the coating to high energy radiation or electron radiation through a photomask, optionally heat treating the exposed coating, and developing the coating with a developer.

* * * * *